US006960659B1

(12) United States Patent
Khudyakov et al.

(10) Patent No.: US 6,960,659 B1
(45) Date of Patent: Nov. 1, 2005

(54) MOSAIC PROTEIN AND RESTRICTION ENDONUCLEASE ASSISTED LIGATION METHOD FOR MAKING THE SAME

(75) Inventors: Yury E. Khudyakov, Duluth, GA (US); Howard A. Fields, Marietta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/491,146

(22) Filed: Jan. 25, 2000

Related U.S. Application Data

(62) Division of application No. 08/921,887, filed on Aug. 25, 1997, now Pat. No. 6,030,771.

(51) Int. Cl.[7] ........................ C07H 21/04; C12N 15/09; C12N 15/51; A61K 39/00; A61K 39/29

(52) U.S. Cl. .................. 536/23.72; 435/69.1; 435/69.3; 435/69.7; 424/192.1; 424/228.1

(58) Field of Search ............................ 536/23.72, 23.4, 536/23.1; 424/229.1, 189.1, 192.1; 435/5, 6, 21, 69.1, 69.3, 69.7; 530/300, 324, 325, 326, 327, 350

(56) References Cited

U.S. PATENT DOCUMENTS

| | | | | |
|---|---|---|---|---|
| 5,106,726 | A | 4/1992 | Wang | |
| 5,302,507 | A | 4/1994 | Chiba et al. | |
| 5,436,126 | A | 7/1995 | Wang | |
| 5,436,318 | A | 7/1995 | Reyes et al. | |
| 5,443,965 | A | 8/1995 | Reyes et al. | |
| 5,538,865 | A | 7/1996 | Reyes et al. | |
| 5,563,032 | A | 10/1996 | Fields et al. | |
| 5,574,132 | A | 11/1996 | Lacroix | |
| 5,625,034 | A | 4/1997 | Liao et al. | |
| 6,428,792 | B1 * | 8/2002 | Valenzuela et al. | 424/228.1 |

FOREIGN PATENT DOCUMENTS

| | | |
|---|---|---|
| AU | 97/05164 | 2/1999 |
| WO | 95/09239 | 4/1995 |
| WO | 95/21858 | 8/1995 |

OTHER PUBLICATIONS

International Committee on the Taxonomy of Viruses, Index of Viruses, at http://www.ictvdb.iacr.ac.uk/ictv/fr–index.htm (Exhibits 1 and 2).*

Division of Viral Hepatitis, Centers for Disease Control and Prevention, "Epidemiology and Prevention of Viral Hepatitis A to E: An Overview," at http://www.cdc.gov/ncidod/diseases/hepatitis/slideset/ .□□*

Kumar et al., "Hepatitis B virus envelope epitopes: gene assembly and expression in Escherichica coli of an immunologically reactive novel multiple–epitope polypeptide 1(MEP–1)," Gene 110:137–144 (1992).*

Yagi et al., "A Epitope Chimeric Anitgen for the Hepatitis C Virus Serological Screening Test," Biol. Pharm. Bull. vol. 19 (10), pp. 1254–1260 (1996).*

Bhattacherjee V, et al., Use of NS–4 peptides to identify type–specific antibody to hepatitis C virus genotypes 1, 2, 3, 4, 5 and 6, Journal of General Virology, 76 (Pt 7) p1737–48, Jul. 1995.*

Maggi et al., Serological Reactivity and Viral Genotypes in Hepatitis C Virus Infection. Journal of Clinical Microbiology 33 (1):p209–211, 1995.*

Nagayama et al., Genotype dependence of hepatitis C virus antibodies detectable bythe first–generation enzyme–linked immunosorbent assay with C100–3protein. Journal of clinical investigation, 92 (3) p1529–33, Sep. 1993.*

Academic Press Dictionary of Science and Technology, On–line, Harcourt, Inc., Definition of "genotype", Sep. 2001.*

"Detection of Antibodies to Hepatitis C Virus (HCV) Structural Proteins in Anti–HCV–Positve Sera by an Enzyme–Linked Immunosorbent Assay Using Synthetic Peptides as Antigens"; *Chuzo Ishida et al. Journal of Clinical Microbiology*, vol. 31, No. 4, Apr. 1993, pp. 936–940.

"E2 and NS5: New Antigens for Detection of Hepatitis C Virus Antibodies"; *H.L. Zaaijer et al., Journal of Medical Virology*, 44:395–397, Apr. 25, 1994.

"Improved Diagnosis of Chronic Hepatitis C Virus Infection by Detection of Antibody to Multiple Epitopes: Confirmation by Antibody to Syunthetic Oligopeptides", *D. Brown et al., Journal of Medical Virology*, 38:167–171, Apr. 3, 1992.

"Preformed Antigen–Antibody Complex to Detect Antibodies to Hepatitis C Virus", *Dinesh Shah, Clinical Chemistry*, vol. 41, No. 9, 1357–58 , 1995.

"Study on Reliability of Commercially Available Hepatitis C Virus Antibody Tests", *H.H. Feucht et al., Journal of Clinical Microbiology*, vol. 33, No. 3, Mar. 1995, pp. 620–624.

"Synthetic gene for the hepatitis C virus nucleocapsid protein", *Y. E. Khudyakov et al., Nucleic Acids Research*, vol. 21, No. 11, pp. 2747–2754, Apr. 30, 1993.

"IgM and IgG Antbodies to Hepatitis E Virus (HEV) Detected by an Enzyme Immunoassay Based on an HEV–Specific Artificial Recombinant Mosaic Protein", *M.O. Favorov, Journal of Medical Virology*, 50:50–58, May 9, 1996.

(Continued)

*Primary Examiner*—James Housel
(74) *Attorney, Agent, or Firm*—Needle & Rosenberg, P.C.

(57) ABSTRACT

A mosaic protein comprising a variety of immunoreactive antigenic epitopes from several genotypes of hepatitis C virus. The mosaic protein provides a sensitive and specific immunological hepatitis detection assay. A restriction enzyme assisted ligation method of making an artificial gene permits controlled construction of mosaic proteins, and allows confirmatory expression of the intermediate gene products.

6 Claims, 25 Drawing Sheets

OTHER PUBLICATIONS

"Artificial Mosaic Protein Containing Antigenic Epitopes of Hepatitis E Virus"; *Yury E. Khudyakov et al., Journal of Virology*, vol. 68, No. 11, Nov. 1994, pp. 7067–7074.

"Solid–phase enzyme–linked immunosorbent assay for hepatitis E virus IgG and IgM antibodies utilizing recombinant antigens and synthetic peptides", *George J. Dawson et al., Journal of Virological Methods*, 38 (1992) pp. 175–186.

"Influence of Viraemia and Genotype Upon Serological Reactivity in Screening Assays for Antibody to Hepatitis C Virus", *S.K. Dhaliwal et al., Journal of Medical Virology*, 48:184–190 (1996).

"Improved serodiagnosis of hepatitis C virus infection with synthetic peptide antigen from capsid protein", *Barbara Hosein et al., Proc. Natl. Acad. Sci. USA*, vol. 88, May 1991, pp. 3647–3651.

"Hepatitis E. virus (HEV): The novel agent responsible for enterically transmitted non–A, non–B hepatitis", *Gregory R. Reyes et al., Gastroenterologia Japonica*, vol. 26, Suppl. 3, Jul. 1991, pp. 142–147.

"T. C or Not to C: These are the Questions", *Harvey J. Alter, Blood*, vol. 85, No. 7, Apr. 1, 1995; pp. 1681–1695.

"Genotype–Dependent Serologic Reactivities in Patients Infected with Hepatitis C Virus in the United States", *Nizar N. Zein, M.D. et al., Mayo Clin. Proc.*, 1995; 70:449–452.

"Improved serologic detection of hepatitis C virus with a paramagnetic microparticle assay using multiple antigenic sequences", *D. Leahy et al., Transufsion*, vol. 32, No. 6, 1992, pp. 548–553.

"Genetic organization and diversity of the hepatitis C virus", *Q.L. Choo et al., Proc. Natl. Acad. Sci. USA*, vol. 88 Mar. 1991, pp. 2451–2455.

Zhang et al., Journal of Medical Virology, 45:50–55, 1995.

Bukh et al., Proc. Natl. Acad. Sci. USA, 91:8239–8243, Aug. 1994.

Chien et al., Proc. Natl. Acad. Sci. USA, 89:10011–10015, Nov. 1992.

Fields et al., Clinical and Diagnostic Virology 5:167–179, 1996.

Ruedinger et al., Abstracts of the 97$^{th}$ General Meeting of the American Society for Microbiology, Abstracts in Clinical and Diagnostic Immunology, # V–54, p. 583.

Khudyakov, Yury et al., "New Frontiers in Protein Engineering: Artificial Mosaic Antigens", 17$^{th}$ International Congress of Biochemistry and Molecular Biology in Conjunction with the Annual Meeting of the American Society for Biochemistry and Molecular Biology, San Francisco, California, USA, Aug. 24–29, 1997, FASEB Journal 11 (9), 1997, abstract No. 1574.

Chokri, Bahoul et al, "DNA–Based Immunization for Exploring the Enlargement of Immunological Cross–Reactivity Against the Lyssaviruses", Vaccine, vol. 16, No. 4, Feb. 1998, pp. 417–425.

* cited by examiner

| Fragment | Sequence | SEQ ID NO |
|---|---|---|
| A | PKPQRKTKRN TIRRPQDVKF PGGGQIVG | 23 |
| B | PKPQRQTKRN TNRRPQDVKF PGGGQIVG | 24 |
| C | PKPQRKTKRN TYRRPQDVKF PGGGQIVG | 25 |
| D | PKPQRKPNRN TNRRPQDVKF PGGGQIVG | 26 |
| E | PKPQRQPKRN TPRRPQDVKF PGGGQIVG | 27 |
| F | PKPQRKTKRN AHRRPQDVKF PGGGQIVG | 28 |
| G | PKPQKRNQRN TNRRPQDVKF PGGGQIVG | 29 |
| H | PKPQRKTKRN TIRRPQDVKF PGGGVIYV | 30 |
| I | PKPQRKTERN TNRRPQDVRF SGGGQIVG | 31 |
| J | PKPKRQTKRN TLRRPKNVKF PAGGQIVG | 32 |
| K | PKPQRKTKRK AHRRPQDVKF PGGGQIVG | 33 |

*FIG. 9*

* PCR, clone, PCR for sequence confirmation and sequential assembly, express, determine immunoreactivity

| | NC Matrix | NS3 Matrix | NS4 Matrix | NS4 Mosaic |
|---|---|---|---|---|
| No. of anti-HCV sera tested | 182 | 182 | 182 | 182 |
| No. of positive sera | 172 | 179 | 158 | 178 |
| Percent positive | 94.5% | 98.4% | 86.8% | 97.8% |

SEQUENCE LISTING

```
<160> NUMBER OF SEQ ID NOS: 55

<210> SEQ ID NO 1
<211> LENGTH: 55
<212> TYPE: DNA
<213> ORGANISM: Hepatitis C virus

<400> SEQUENCE: 1

ccccgaattc aaccgaaacc gcaacgtaaa accaaacgta acaccattcg tcgtc          55


<210> SEQ ID NO 2
<211> LENGTH: 69
<212> TYPE: DNA
<213> ORGANISM: Hepatitis C virus

<400> SEQUENCE: 2

ccccggatcc tatttcggac caacgatctg accaccaccc gggaatttaa cgtcctgcgg     60

acgacgaat                                                             69


<210> SEQ ID NO 3
<211> LENGTH: 54
<212> TYPE: DNA
<213> ORGANISM: Hepatitis C virus

<400> SEQUENCE: 3

ccccgaattc aaccgaaacc gcaacgtcag accaaacgta acaccaaccg tcgt           54


<210> SEQ ID NO 4
<211> LENGTH: 70
<212> TYPE: DNA
<213> ORGANISM: Hepatitis C virus

<400> SEQUENCE: 4

ccccggatcc tatttcggac caacgatctg accaccaccc gggaatttaa cgtcctgcgg     60

acgacggttg                                                            70
```

-continued

<210> SEQ ID NO 5
<211> LENGTH: 51
<212> TYPE: DNA
<213> ORGANISM: Hepatitis C virus

<400> SEQUENCE: 5
ccccgaattc aaccgaaacc gcaacgtaaa accaaacgta acacctaccg t 51

<210> SEQ ID NO 6
<211> LENGTH: 73
<212> TYPE: DNA
<213> ORGANISM: Hepatitis C virus

<400> SEQUENCE: 6
ccccggatcc tatttcggac caacgatctg accaccaccc gggaatttaa cgtcctgcgg 60
acgacggtag gtg 73

<210> SEQ ID NO 7
<211> LENGTH: 55
<212> TYPE: DNA
<213> ORGANISM: Hepatitis C virus

<400> SEQUENCE: 7
ccccgaattc aaccgaaacc gcaacgtaaa ccgaaccgta acaccaaccg tcgtc 55

<210> SEQ ID NO 8
<211> LENGTH: 69
<212> TYPE: DNA
<213> ORGANISM: Hepatitis C virus

<400> SEQUENCE: 8
ccccggatcc tatttcggac caacgatctg accaccaccc gggaatttaa cgtcctgcgg 60
acgacggtt 69

<210> SEQ ID NO 9
<211> LENGTH: 63
<212> TYPE: DNA
<213> ORGANISM: Hepatitis C virus

<400> SEQUENCE: 9
ccccgaattc aaccgaaacc gcaacgtcag ccgaaacgta acaccccgcg tcgtccgcag 60
gac 63

<210> SEQ ID NO 10
<211> LENGTH: 60
<212> TYPE: DNA
<213> ORGANISM: Hepatitis C virus

<400> SEQUENCE: 10
ccccggatcc tatttcggac caacgatctg accaccaccc gggaatttaa cgtcctgcgg 60

<210> SEQ ID NO 11
<211> LENGTH: 55
<212> TYPE: DNA
<213> ORGANISM: Hepatitis C virus

<400> SEQUENCE: 11
ccccgaattc aaccgaaacc gcaacgtaaa accaaacgta acgctcaccg tcgtc 55

<210> SEQ ID NO 12
<211> LENGTH: 69

-continued

<212> TYPE: DNA
<213> ORGANISM: Hepatitis C virus

<400> SEQUENCE: 12
ccccggatcc tatttcggac caacgatctg accaccaccc gggaatttaa cgtcctgcgg 60
acgacggtg 69

<210> SEQ ID NO 13
<211> LENGTH: 55
<212> TYPE: DNA
<213> ORGANISM: Hepatitis C virus

<400> SEQUENCE: 13
ccccgaattc aaccgaaacc gcaacgtaaa aaccagcgta acaccaaccg tcgtc 55

<210> SEQ ID NO 14
<211> LENGTH: 69
<212> TYPE: DNA
<213> ORGANISM: Hepatitis C virus

<400> SEQUENCE: 14
ccccggatcc tatttcggac caacgatctg accaccaccc gggaatttaa cgtcctgcgg 60
acgacggtt 69

<210> SEQ ID NO 15
<211> LENGTH: 55
<212> TYPE: DNA
<213> ORGANISM: Hepatitis C virus

<400> SEQUENCE: 15
ccccgaattc aaccgaaacc gcaacgtaaa accaaacgta acaccattcg tcgtc 55

<210> SEQ ID NO 16
<211> LENGTH: 69
<212> TYPE: DNA
<213> ORGANISM: Hepatitis C virus

<400> SEQUENCE: 16
ccccggatcc tatttcggaa cgtagataac accaccaccc gggaatttaa cgtcctgcgg 60
acgacgaat 69

<210> SEQ ID NO 17
<211> LENGTH: 56
<212> TYPE: DNA
<213> ORGANISM: Hepatitis C virus

<400> SEQUENCE: 17
ccccgaattc aaccgaaacc gcaacgtaaa accgaacgta acaccaaccg tcgtcc 56

<210> SEQ ID NO 18
<211> LENGTH: 65
<212> TYPE: DNA
<213> ORGANISM: Hepatitis C virus

<400> SEQUENCE: 18
ccccggatcc tatttcggac caacgatctg accaccacca gagaaacgaa cgtccggacg 60
acggt 65

<210> SEQ ID NO 19
<211> LENGTH: 54
<212> TYPE: DNA

-continued

<213> ORGANISM: Hepatitis C virus

<400> SEQUENCE: 19
ccccgaattc aaccgaaacc gaaacgtcag accaaacgta acaccctgcg tcgt 54

<210> SEQ ID NO 20
<211> LENGTH: 73
<212> TYPE: DNA
<213> ORGANISM: Hepatitis C virus

<400> SEQUENCE: 20
ccccggatcc tatttcggac caacgatctg accaccagcc gggaatttaa cgtttttcgg 60
acgacgacgc agg 73

<210> SEQ ID NO 21
<211> LENGTH: 55
<212> TYPE: DNA
<213> ORGANISM: Hepatitis C virus

<400> SEQUENCE: 21
ccccgaattc aaccgaaacc gcaacgtaaa accaaacgta aagctcaccg tcgtc 55

<210> SEQ ID NO 22
<211> LENGTH: 69
<212> TYPE: DNA
<213> ORGANISM: Hepatitis C virus

<400> SEQUENCE: 22
ccccggatcc tatttcggac caacgatctg accaccaccc gggaatttaa cgtcctgcgg 60
acgacggtg 69

<210> SEQ ID NO 23
<211> LENGTH: 28
<212> TYPE: PRT
<213> ORGANISM: Hepatitis C virus

<400> SEQUENCE: 23

```
Pro Lys Pro Gln Arg Lys Thr Lys Arg Asn Thr Ile Arg Arg Pro Gln
 1               5                  10                  15

Asp Val Lys Phe Pro Gly Gly Gly Gln Ile Val Gly
            20                  25
```

<210> SEQ ID NO 24
<211> LENGTH: 28
<212> TYPE: PRT
<213> ORGANISM: Hepatitis C virus

<400> SEQUENCE: 24

```
Pro Lys Pro Gln Arg Gln Thr Lys Arg Asn Thr Asn Arg Arg Pro Gln
 1               5                  10                  15

Asp Val Lys Phe Pro Gly Gly Gly Gln Ile Val Gly
            20                  25
```

<210> SEQ ID NO 25
<211> LENGTH: 28
<212> TYPE: PRT
<213> ORGANISM: Hepatitis C virus

<400> SEQUENCE: 25

```
Pro Lys Pro Gln Arg Lys Thr Lys Arg Asn Thr Tyr Arg Arg Pro Gln
 1               5                  10                  15
```

-continued

```
Asp Val Lys Phe Pro Gly Gly Gly Gln Ile Val Gly
            20                  25
```

<210> SEQ ID NO 26
<211> LENGTH: 28
<212> TYPE: PRT
<213> ORGANISM: Hepatitis C virus

<400> SEQUENCE: 26

```
Pro Lys Pro Gln Arg Lys Pro Asn Arg Asn Thr Asn Arg Arg Pro Gln
 1               5                  10                  15

Asp Val Lys Phe Pro Gly Gly Gly Gln Ile Val Gly
            20                  25
```

<210> SEQ ID NO 27
<211> LENGTH: 28
<212> TYPE: PRT
<213> ORGANISM: Hepatitis C virus

<400> SEQUENCE: 27

```
Pro Lys Pro Gln Arg Gln Pro Lys Arg Asn Thr Pro Arg Arg Pro Gln
 1               5                  10                  15

Asp Val Lys Phe Pro Gly Gly Gly Gln Ile Val Gly
            20                  25
```

<210> SEQ ID NO 28
<211> LENGTH: 28
<212> TYPE: PRT
<213> ORGANISM: Hepatitis C virus

<400> SEQUENCE: 28

```
Pro Lys Pro Gln Arg Lys Thr Lys Arg Asn Ala His Arg Arg Pro Gln
 1               5                  10                  15

Asp Val Lys Phe Pro Gly Gly Gly Gln Ile Val Gly
            20                  25
```

<210> SEQ ID NO 29
<211> LENGTH: 28
<212> TYPE: PRT
<213> ORGANISM: Hepatitis C virus

<400> SEQUENCE: 29

```
Pro Lys Pro Gln Lys Arg Asn Gln Arg Asn Thr Asn Arg Arg Pro Gln
 1               5                  10                  15

Asp Val Lys Phe Pro Gly Gly Gly Gln Ile Val Gly
            20                  25
```

<210> SEQ ID NO 30
<211> LENGTH: 28
<212> TYPE: PRT
<213> ORGANISM: Hepatitis C virus

<400> SEQUENCE: 30

```
Pro Lys Pro Gln Arg Lys Thr Lys Arg Asn Thr Ile Arg Arg Pro Gln
 1               5                  10                  15

Asp Val Lys Phe Pro Gly Gly Gly Val Ile Tyr Val
            20                  25
```

<210> SEQ ID NO 31
<211> LENGTH: 28
<212> TYPE: PRT
<213> ORGANISM: Hepatitis C virus -continued

<400> SEQUENCE: 31

Pro Lys Pro Gln Arg Lys Thr Glu Arg Asn Thr Asn Arg Arg Pro Gln
1 5 10 15

Asp Val Arg Phe Ser Gly Gly Gly Gln Ile Val Gly
20 25

<210> SEQ ID NO 32
<211> LENGTH: 28
<212> TYPE: PRT
<213> ORGANISM: Hepatitis C virus

<400> SEQUENCE: 32

Pro Lys Pro Lys Arg Gln Thr Lys Arg Asn Thr Leu Arg Arg Pro Lys
1 5 10 15

Asn Val Lys Phe Pro Ala Gly Gly Gln Ile Val Gly
20 25

<210> SEQ ID NO 33
<211> LENGTH: 28
<212> TYPE: PRT
<213> ORGANISM: Hepatitis C virus

<400> SEQUENCE: 33

Pro Lys Pro Gln Arg Lys Thr Lys Arg Lys Ala His Arg Arg Pro Gln
1 5 10 15

Asp Val Lys Phe Pro Gly Gly Gly Gln Ile Val Gly
20 25

<210> SEQ ID NO 34
<211> LENGTH: 82
<212> TYPE: DNA
<213> ORGANISM: Hepatitis C virus

<400> SEQUENCE: 34
ccccgaattc aagccgccca cataccatac ctagaacaag gaatgcatct cgcagaacaa 60
ttcaaacaaa aggcacttcg tc 82

<210> SEQ ID NO 35
<211> LENGTH: 84
<212> TYPE: DNA
<213> ORGANISM: Hepatitis C virus

<400> SEQUENCE: 35
ccccggatcc taactagcct cttccatctc atcaaactcc tgatacaaaa cctccctatc 60
cgggataaca gccggacgaa gtgc 84

<210> SEQ ID NO 36
<211> LENGTH: 85
<212> TYPE: DNA
<213> ORGANISM: Hepatitis C virus

<400> SEQUENCE: 36
ccccgaattc aagctagtca cttaccgtat atcgagcagg gaatgcagtt agctgaacag 60
tttaaacaga aggctctggc ttttg 85

<210> SEQ ID NO 37
<211> LENGTH: 81
<212> TYPE: DNA
<213> ORGANISM: Hepatitis C virus

<400> SEQUENCE: 37

-continued

```
ccccggatcc taaggccgag cgtcagactc aggaacataa tgagtaggag aaacatgatt     60

accccgagaa gcaaaagcca g                                               81


<210> SEQ ID NO 38
<211> LENGTH: 81
<212> TYPE: DNA
<213> ORGANISM: Hepatitis C virus

<400> SEQUENCE: 38

ccccgaattc aacggcctgc gataataccg gatagggagg ttcttcatag ggagtttgac     60

gagatggagg aggcttttgc g                                               81


<210> SEQ ID NO 39
<211> LENGTH: 79
<212> TYPE: DNA
<213> ORGANISM: Hepatitis C virus

<400> SEQUENCE: 39

ccccggatcc tactgcgaag catcagactc aggaacataa tgagccggac taacatgatt     60

cccacgagac gcaaaagcc                                                  79


<210> SEQ ID NO 40
<211> LENGTH: 83
<212> TYPE: DNA
<213> ORGANISM: Hepatitis C virus

<400> SEQUENCE: 40

ccccgaattc aatcgcaggc ggcgccttat attgagcagg ctcaggttat tgctcatcag     60

tttaaggaga aggttcttgc ttt                                             83


<210> SEQ ID NO 41
<211> LENGTH: 83
<212> TYPE: DNA
<213> ORGANISM: Hepatitis C virus

<400> SEQUENCE: 41

ccccggatcc tacggcttcg cgtccgactc aggaacataa tgagtcggag aatcatgatt     60

accacgagaa gcaaaagcaa gaa                                             83


<210> SEQ ID NO 42
<211> LENGTH: 79
<212> TYPE: DNA
<213> ORGANISM: Hepatitis C virus

<400> SEQUENCE: 42

ccccgaattc aaaagccggc gataatccct gaccgtgagg ttctgtatcg tgagtttgat     60

gagatggagg agtcacagc                                                  79


<210> SEQ ID NO 43
<211> LENGTH: 87
<212> TYPE: DNA
<213> ORGANISM: Hepatitis C virus

<400> SEQUENCE: 43

ccccggatcc taaaacgcca gagccttctg cttaaactgc tcagcaagca tcataccctg     60

ctcaatgtac ggaagatgct gtgactc                                         87


<210> SEQ ID NO 44
```

-continued

<211> LENGTH: 76
<212> TYPE: DNA
<213> ORGANISM: Hepatitis C virus

<400> SEQUENCE: 44
ccccgaattc aagcgtttgc ttctcgtggt aatcatgttg ctccgactca ttatgttacg 60
gagtcagatg ctaagc 76

<210> SEQ ID NO 45
<211> LENGTH: 84
<212> TYPE: DNA
<213> ORGANISM: Hepatitis C virus

<400> SEQUENCE: 45
ccccggatcc tagaaagcct cctccatctc atcatactgc tgataaagaa cctccttatc 60
cggaaccaga gccggcttag catc 84

<210> SEQ ID NO 46
<211> LENGTH: 80
<212> TYPE: DNA
<213> ORGANISM: Hepatitis C virus

<400> SEQUENCE: 46
ccccgaattc aagctttcgc ttctcgtggt aatcatgttg ctcctacgca ttatgttgtt 60
gagtcagatg cttctgcttc 80

<210> SEQ ID NO 47
<211> LENGTH: 86
<212> TYPE: DNA
<213> ORGANISM: Hepatitis C virus

<400> SEQUENCE: 47
ccccggatcc tagaaagcca gaaccttctc cttaaactga ccagcaatag cacgcgtctc 60
gtccatatac ggcagagaag cagaag 86

<210> SEQ ID NO 48
<211> LENGTH: 80
<212> TYPE: DNA
<213> ORGANISM: Hepatitis C virus

<400> SEQUENCE: 48
ccccgaattc aagctttcgc tagtcgtggg aatcatgtgt cgccgcgtca ttatgtgcct 60
gagtctgagc ctcaggttgt 80

<210> SEQ ID NO 49
<211> LENGTH: 80
<212> TYPE: DNA
<213> ORGANISM: Hepatitis C virus

<400> SEQUENCE: 49
ccccggatcc taagaagcct cctccatctc atcaaaagcc tcatacagta tctccttatc 60
cggcgtaaca acaacctgag 80

<210> SEQ ID NO 50
<211> LENGTH: 52
<212> TYPE: DNA
<213> ORGANISM: Hepatitis C virus

<400> SEQUENCE: 50
ccccgaattc aagcttctaa ggccgcgctg attgaggagg gtcagcgtat gg 52

-continued

<210> SEQ ID NO 51
<211> LENGTH: 48
<212> TYPE: DNA
<213> ORGANISM: Hepatitis C virus

<400> SEQUENCE: 51
ccccggatcc tactggatct tagacttcag catctcagcc atacgctg 48

<210> SEQ ID NO 52
<211> LENGTH: 352
<212> TYPE: PRT
<213> ORGANISM: Hepatitis C virus

<400> SEQUENCE: 52

```
Ala Ala His Ile Pro Tyr Leu Glu Gln Gly Met His Leu Ala Glu Gln
 1               5                  10                  15

Phe Lys Gln Lys Ala Leu Arg Pro Ala Val Ile Pro Asp Arg Glu Val
            20                  25                  30

Leu Tyr Gln Glu Phe Asp Glu Met Glu Glu Ala Ser His Leu Pro Tyr
        35                  40                  45

Ile Glu Gln Gly Met Gln Leu Ala Glu Gln Phe Lys Gln Lys Ala Leu
    50                  55                  60

Ala Phe Ala Ser Arg Gln Asn His Val Ser Pro Thr His Tyr Val Pro
 65                  70                  75                  80

Glu Ser Asp Ala Arg Pro Ala Ile Ile Pro Asp Arg Glu Val Leu His
                85                  90                  95

Arg Glu Phe Asp Glu Met Glu Glu Ala Phe Ala Ser Arg Gly Asn His
            100                 105                 110

Val Ser Pro Ala His Tyr Val Pro Glu Ser Asp Ala Ser Gln Ala Ala
        115                 120                 125

Pro Tyr Ile Glu Gln Ala Gln Val Ile Ala His Gln Phe Lys Glu Lys
    130                 135                 140

Val Leu Ala Phe Ala Ser Arg Gly Asn His Asp Ser Pro Thr His Tyr
145                 150                 155                 160

Val Pro Glu Ser Asp Ala Lys Pro Ala Ile Ile Pro Asp Arg Glu Val
                165                 170                 175

Leu Tyr Arg Glu Phe Asp Glu Met Glu Glu Ser Gln His Leu Pro Tyr
            180                 185                 190

Ile Glu Gln Gly Met Met Leu Ala Glu Gln Phe Lys Gln Lys Ala Leu
        195                 200                 205

Ala Phe Ala Ser Arg Gly Asn His Val Ala Pro Thr His Tyr Val Thr
    210                 215                 220

Glu Ser Asp Ala Lys Pro Ala Leu Val Pro Asp Lys Glu Val Leu Tyr
225                 230                 235                 240

Gln Gln Tyr Asp Glu Met Glu Glu Ala Phe Ala Ser Arg Gly Asn His
                245                 250                 255

Val Ala Pro Thr His Tyr Val Val Glu Ser Asp Ala Ser Ala Ser Leu
            260                 265                 270

Pro Tyr Met Asp Glu Thr Arg Ala Ile Ala Gly Gln Phe Lys Glu Lys
        275                 280                 285

Val Leu Ala Phe Ala Ser Arg Gly Asn His Val Ser Pro Arg His Tyr
    290                 295                 300

Val Pro Glu Ser Glu Pro Gln Val Val Val Thr Pro Asp Lys Glu Ile
305                 310                 315                 320
```

-continued

```
Leu Tyr Glu Ala Phe Asp Glu Met Glu Glu Ala Ser Lys Ala Ala Leu
            325                 330                 335

Ile Glu Glu Gly Gln Arg Met Ala Glu Met Leu Lys Ser Lys Ile Gln
        340                 345                 350


<210> SEQ ID NO 53
<211> LENGTH: 57
<212> TYPE: DNA
<213> ORGANISM: Hepatitis C virus

<400> SEQUENCE: 53

ctggttccgc gtggatcccc aggaattccc gggtcgactc gagcggccgc atcgtga        57


<210> SEQ ID NO 54
<211> LENGTH: 27
<212> TYPE: DNA
<213> ORGANISM: Hepatitis C virus

<400> SEQUENCE: 54

tcgcagcgaa ttctcgagga tccatcc                                         27


<210> SEQ ID NO 55
<211> LENGTH: 55
<212> TYPE: DNA
<213> ORGANISM: Hepatitis C virus

<400> SEQUENCE: 55

ctggttccgc gtggatcgca gcgaattctc gaggatccat ccggccgcat cgtga          55
```

MOSAIC PROTEIN AND RESTRICTION ENDONUCLEASE ASSISTED LIGATION METHOD FOR MAKING THE SAME

The present application is a 37 C.F.R. § 1.53(b) divisional of, and which claims priority to, U.S. patent application Ser. No. 08/921,887, filed Aug. 25, 1997, which issued as U.S. Pat. No. 6,030,771 on Feb. 29, 2000, which application is hereby incorporated herein in its entirety.

FIELD OF THE INVENTION

The present invention relates to the field of recombinant production of proteins from synthetic genes. In particular, the invention relates to the expression of mosaic proteins constructed from antigenic peptides of the hepatitis C virus.

BACKGROUND OF THE INVENTION

The hepatitis C virus (HCV) is classified as part of the Flaviviridae family, and contains a single, positive strand of RNA approximately 9400 nucleotides long, encoding for at least a 3000 amino acid polyprotein, depending on the source of the viral isolate. (Choo Q-L., et al., *Proc. Natl. Acad. Sci. USA* 88:2451–2455, 1991; Choo Q-L., et al., *Science* 244:359–362, 1989; Kato N., et al., *Proc. Natl. Acad. Sci. USA* 87:9524–9528, 1990; Takamizawa A., et al., *J. Virol.* 65:1105–1113, 1991) The 5'-end of the genome encodes for the structural proteins that include the nucleocapsid protein (C), and two envelope proteins (E1, and E2/NS1), whereas the 3'-end of the genome encodes for the non-structural proteins that include the NS2, NS3, NS4, and NS5 proteins. (Miller R. H. and Purcell R. H., *Proc. Natl. Acad. Sci. USA* 87:2057–2061, 1990; Takeuchi K., et al., *J. Gen. Virol.* 71:3027–3033, 1990; Choo Q-L., et al., *Proc. Natl. Acad. Sci. USA* 88:2451–2455, 1991; Hijikata M., et al., *Proc. Natl. Acad. Sci. USA* 88:5547–5551, 1991; Takamizawa A., et al., *J. Virol.* 65:1105–1113, 1991; Houghton M., et al., *Hepatology* 14:381–388, 1991) The hepatitis C virus is the main causative agent of non-A, non-B hepatitis, and plays a major role in the development of chronic liver disease, liver cirrhosis, and hepatocellular carcinoma worldwide. (Choo Q-L, et al., *Proc. Natl. Acad. Sci. USA* 88:2451–2455, 1991) Since there is no vaccine and no effective therapy for HCV induced disease, diagnosis and prevention of infection are issues of major public health importance.

In an effort to improve the efficiency of HCV diagnosis, many antigenic regions have been identified along the HCV genome, and used to develop three generations of enzyme immunoassays for the detection of anti-HCV activity in human sera. (Kuo et al., *Science* 244:362–364, 1989; Chien D. Y., et al., *Proc. Natl. Acad. Sci. USA* 89:10011–10015, 1992) Each successive generation represented an improvement in both the sensitivity and specificity of the enzyme immunoassay (EIA) by adding more antigenic regions to the assay. The first generation of enzyme immunoassays relied on the detection of antibodies to a region within a non-structural protein, 5-1-1. Second and third generation assays were based on the detection of antibodies against the recombinant 22 kDa core or nucleocapsid (NC) protein and several recombinant proteins derived from non-structural regions of the viral polyprotein (NS3, NS4, NS5).

Although the improvements in the specificity and sensitivity of the EIAs have resulted in a reduction in the number of new HCV infections (Alter H. J., *Blood* 85(7):1681–1695, 1995), many investigators have indicated that the current versions still require further development. (Tobler L. H., et al., *Transfusion* 34:130–134, 1994; Courouce A. M., et al., *Transfusion* 34:790–795, 1994; Damen M., et al., *Transfusion* 35:745–749, 1995; Feucht H. H., et al., *J. Med Virol.* 48:184–190, 1995; Bar-Shany S., et al., *Inetrnl. J. Epi.* 25:674–677, 1996; Dhaliwal S. K., et al., *J. Med. Virol.* 48:184–190, 1996; Pawlotsky J. M., et al., *J. Clin. Micro.* Jan:80–83, 1996) The impetus to improve tests for detection of anti-HCV is based upon studies demonstrating that currently available EIAs have relatively poor specificities, especially in low-prevalence populations. (Alter H. J., *Blood* 85(7):1681–1695, 1995; Feucht H. H., et al., *J. Med. Virol.* 48:184–190, 1995) Additionally, even after the development of supplemental tests, such as MATRIX immunoassay (Abbott Laboratories, Abbott Park, Ill.), used to confirm EIA positive sera, 10% of specimens are still classified as indeterminate (reactive to a single antigen) following supplemental testing. (Pawlotsky J. M., et al., *J. Clin. Micro.* Jan:80–83, 1996) These findings might be due to testing sera during the very early stage of infection before all antibodies reach detectable levels. Alternatively, reactivity to a single antigen may be due to non-specificity of the specimen.

Another important limitation to currently available assays is the use of genotype 1 recombinant proteins as immunologic targets. Recently, it was reported that there are differences in the serologic reactivity of the current EIAs to the different HCV genotypes. (Zein N. N., et al., *Mayo Clinic Proc.* 70(5):449–452, 1995; Dhaliwal S. K., et al., *J. Med. Virol.* 48:184–190, 1996) This observation suggests that the current EIAs, which are based on type I HCV, may need to be further improved by including antigenic epitopes from different genotypes. Therefore, it is clear that there remains a strong need for an enzyme immunoassay with increased specificity and sensitivity that would react with sera infected with multiple genotypes of the hepatitis C virus.

To create an enzyme immunoassay with broad reactivity to multiple genotypes, a synthetic protein must be assembled from a long DNA fragment containing multiple antigenic epitopes. The synthesis of long artificial DNA polynucleotides has been made possible by the availability of highly efficient methods to chemically synthesize relatively short oligonucleotides. To assemble a gene from oligonucleotides, several enzymatic reactions using polymerases and/or ligases may be used. Two methods described elsewhere (Khudyakov Y. E., et al., *Nucleic Acid Res.* 21(11):2747–2754, 1993; Khudyakov Y. E., et al., *J. Virol.* 68:(11) 7067–7074, 1994; and U.S. Pat. No. 5,563,032), the polymerase chain reaction (PCR) and the Exchangeable Template Reaction (ETR), have been successfully applied to assemble synthetic genes from oligonucleotides. The use of PCR, however, is disadvantageous in cases where repeated sequences are designed in the gene, while ETR can not be used to conveniently express short fragments of the synthetic gene. Therefore, a new method of assembling synthetic genes with repeated sequences that would allow for the expression of shorter fragments of the gene, would greatly facilitate the creation of a synthetic protein to be used in an improved enzyme immunoassay, in particular for the detection of HCV.

SUMMARY OF THE INVENTION

The present invention relates to methods and compositions used to improve the sensitivity, the spectrum of immunoreactivity, and the specificity of antigens used as immunologic targets for detection. In preferred embodiments, the detection can be performed by enzyme immunoassay (EIA). The method, designated Restriction Endonuclease Assisted Ligation (REAL), involves the construction of an artificial gene from synthetic oligonucleotides. The compositions are synthetic proteins composed of a mosaic of broadly immunoreactive antigenic epitopes from several genotypes of, for example HCV.

REAL employs the use of the Klenow fragment of DNA Polymerase I to convert specially designed complimentary oligonucleotides into double stranded DNA fragments, which are subsequently amplified by PCR. Restriction sites were engineered into the cloning vector and used to produce complimentary overhangs for the addition of consecutive fragments. Each fragment may be cloned and expressed individually, for example in *Escherichia coli* to determine their immunoreactivity or may be assembled into full length product without cloning. Two consecutive fragments are subsequently ligated, amplified by PCR, cleaved with restriction endonucleases, and ligated with DNA ligase to assemble each fragment into a longer fragment in a consecutive process. By repeating this process fragments of increasing length are assembled, expressed and analyzed for immunoreactivity, and reiterated until the full length gene is assembled.

The invention provides mosaic proteins comprising a plurality of homologous antigenic peptides from different genotypes of a hepatitis virus. In particular, the invention provides mosaic proteins comprising a plurality of homologous antigenic nucleocapsid peptides from different genotypes of a hepatitis C virus. Further, the invention provides mosaic proteins comprising a plurality of homologous antigenic non-structural peptides from different genotypes of a hepatitis C virus. The mosaic proteins and genes encoding therefor can be used for immunologic detection or vaccination.

BRIEF DESCRIPTION OF THE FIGURES

FIG. 9 shows the amino acid sequence of each monomer comprising the NC mosaic protein. The bolded amino acids indicate the variations between the sequences of each monomer.

FIG. 23 shows a comparison of the percent positively for anti-NS3, anti-NS4, and anti-NC activity by MATRIX immunoassay versus anti-NS4 activity by NS4 Mosaic EIA using 182 anti-HCV positive sera.

DETAILED DESCRIPTION

Figure 1:
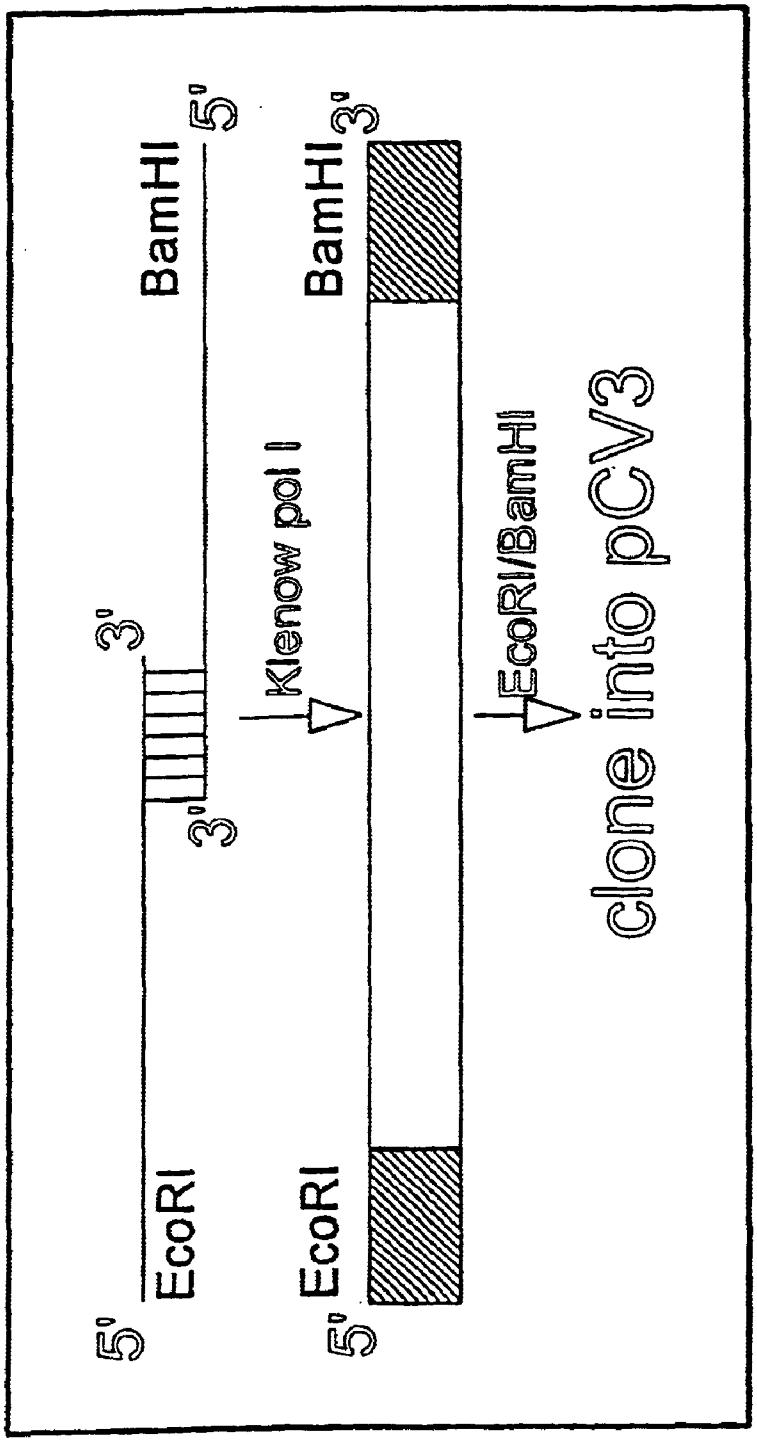
FIG. 1 is a schematic representation of the strategy used to insert each monomer into the cloning vector. Monomers were cloned into EcoRI and BamHI treated vector pCV3 by treatment of annealed oligonucleotides with the Klenow fragment of DNA Polymerase I followed by restriction endonuclease cleavage.

The present invention relates to methods and compositions used to improve the sensitivity, the spectrum of immunoreactivity, and the specificity of antigens used as immunologic targets for detection. In preferred embodiments, the detection can be performed by enzyme immunoassay (EIA). The method, designated Restriction Endonuclease Assisted Ligation (REAL), involves the construction of an artificial gene from synthetic oligonucleotides. The compositions are synthetic proteins composed of a mosaic of broadly immunoreactive antigenic epitopes from several genotypes of a species, for example hepatitis C virus (HCV). The mosaic protein compositions can be used for immunologic detection of, or vaccination against, the organisms from which they are derived. The invention further contemplates that the nucleic acids encoding the mosaic proteins can be used for immunologic detection of, or vaccination against, the organisms from which they are derived. Therefore, in addition to compositions and methods for detecting hepatitis, the invention provides a hepatitis vaccine comprising a mosaic protein, or a gene encoding therefor.

REAL employs the use of the Klenow fragment of DNA Polymerase I to convert specially designed complimentary oligonucleotides into double stranded DNA fragments, which are subsequently amplified by PCR. Restriction sites were engineered into the cloning vector and used to produce complimentary overhangs for the addition of consecutive fragments. Each fragment may be cloned and expressed individually, for example in *Escherichia coli* to determine their immunoreactivity or may be assembled into full length product without cloning. Two consecutive fragments are subsequently ligated, amplified by PCR, cleaved with restriction endonucleases, and ligated with DNA ligase to assemble each fragment into a longer fragment in a consecutive process. By repeating this process fragments of increasing length are assembled, expressed and analyzed for immunoreactivity, and reiterated until the full length gene is assembled.

In particular, the present invention provides a method of constructing an artificial gene, comprising synthesizing an initial oligonucleotide containing an initial gene segment encoding an initial gene product. The initial gene segment is flanked in the upstream direction (5') by an upstream initial ligating sequence, a first endonuclease recognition sequence that is recognized by a first endonuclease that cleaves at the first endonuclease recognition sequence, and a second endonuclease recognition sequence which is recognized by a second endonuclease that cleaves downstream of the first endonuclease recognition sequence and within the upstream initial ligating sequence.

Additionally, the initial gene segment is flanked in the downstream direction (3') by a downstream initial ligating sequence, a stop codon, a third endonuclease recognition sequence that is recognized by a third endonuclease that cleaves at the third endonuclease recognition sequence, and a fourth endonuclease recognition sequence which is recognized by a fourth endonuclease that cleaves upstream of the third endonuclease recognition sequence, upstream of the stop codon, and within the downstream initial ligating sequence. An example of such an initial oligonucleotide can be seen in FIG. 4, wherein "SEGMENT" designates the initial gene segment and "NNNNNN" designates the initial ligating sequence.

The method further comprises synthesizing a subsequent oligonucleotide containing a subsequent gene segment encoding a subsequent gene product. The subsequent gene segment is flanked in the upstream direction (5') by an upstream subsequent ligating sequence, a first endonuclease recognition sequence which is recognized by the first endonuclease that cleaves at the first endonuclease recognition sequence, and a second endonuclease recognition sequence which is recognized by the second endonuclease that cleaves downstream of the first endonuclease recognition sequence and within the upstream subsequent ligating sequence.

The subsequent gene segment is flanked in the downstream direction (3') by a downstream subsequent ligating sequence, a stop codon, a third endonuclease recognition sequence which is recognized by the third endonuclease that cleaves at the third endonuclease recognition sequence, and a fourth endonuclease recognition sequence which is recognized by the fourth endonuclease that cleaves upstream of the third endonuclease recognition sequence, upstream of the stop codon, and within the downstream subsequent ligating sequence. An example of such an subsequent oligonucleotide can be seen in FIG. 4, wherein "SEGMENT" designates the subsequent gene segment and "NNNNNN" designates the subsequent ligating sequence.

Figure 6:
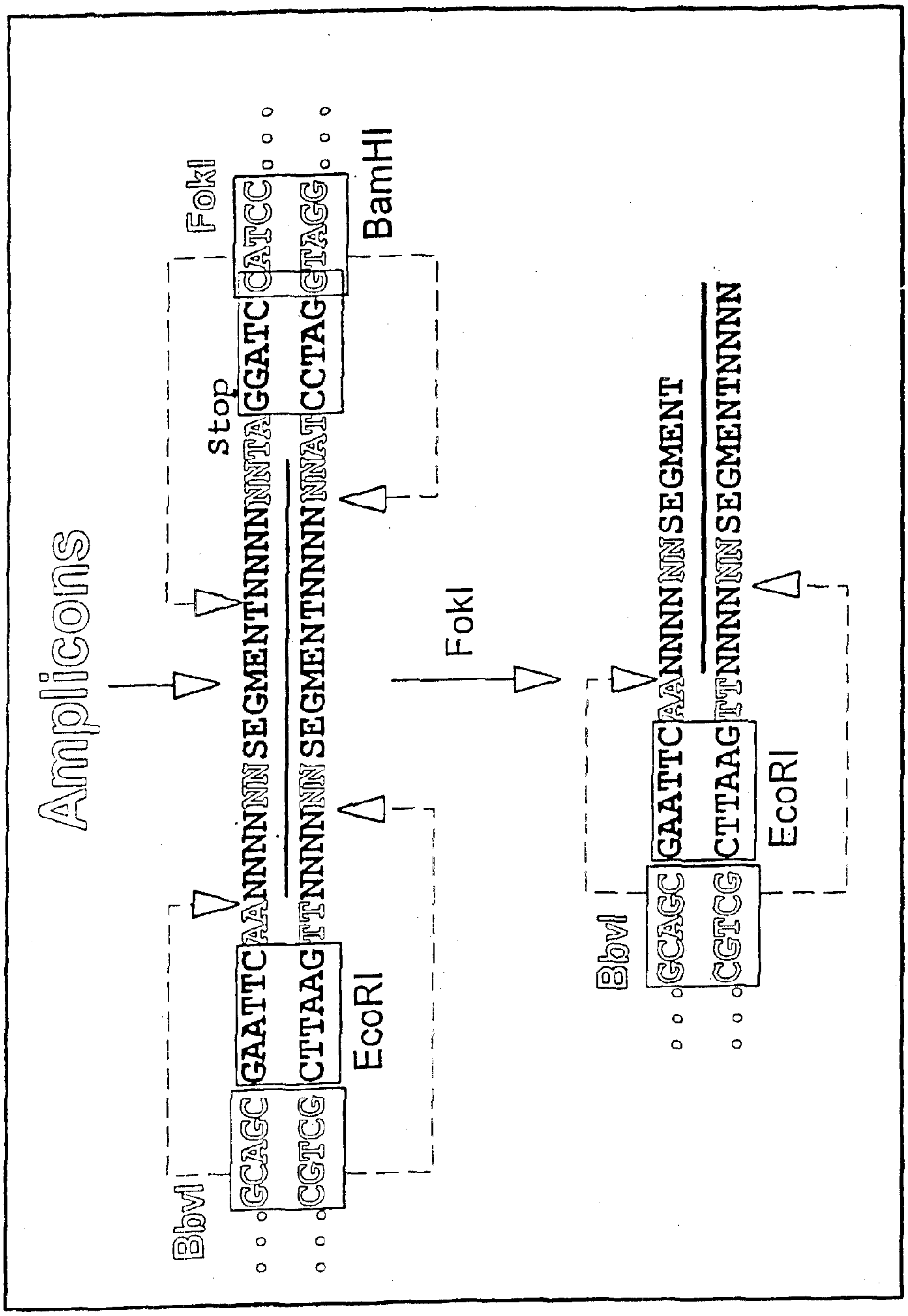
FIG. 6 is a schematic representation of the PCR amplicons containing BbvI, EcoRI, BamHI, and FokI restriction sites, and the subsequent restriction of the first monomer with the FokI restriction enzyme.
Figure 7:
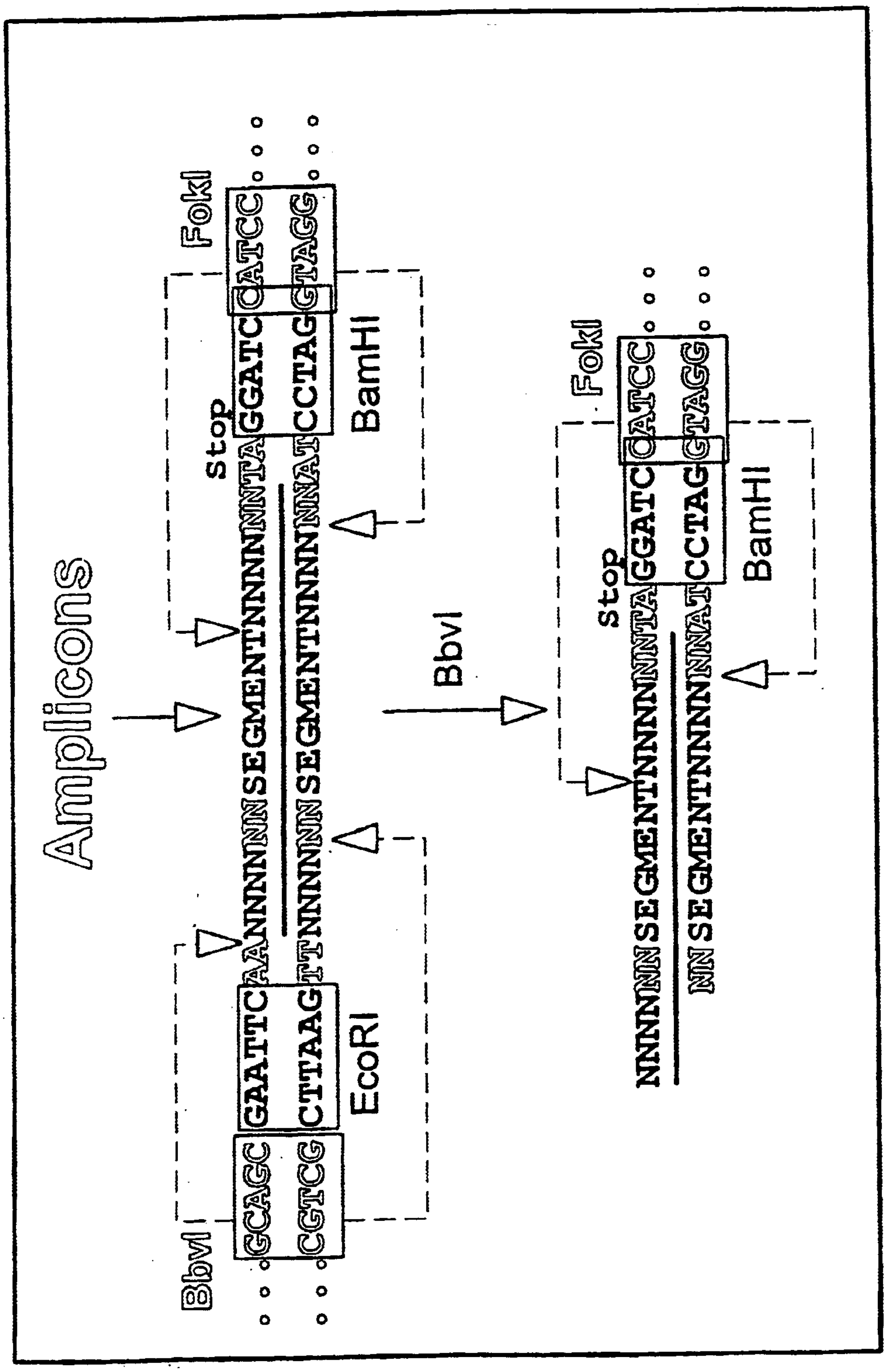
FIG. 7 shows the restriction of a second consecutive monomer with the BbvI restriction enzyme.

The method further comprises the step of cleaving the initial oligonucleotide with the fourth endonuclease, and cleaving the subsequent oligonucleotide with the second endonuclease. An example of this step is shown in FIGS. 6 and 7.

Figure 8:
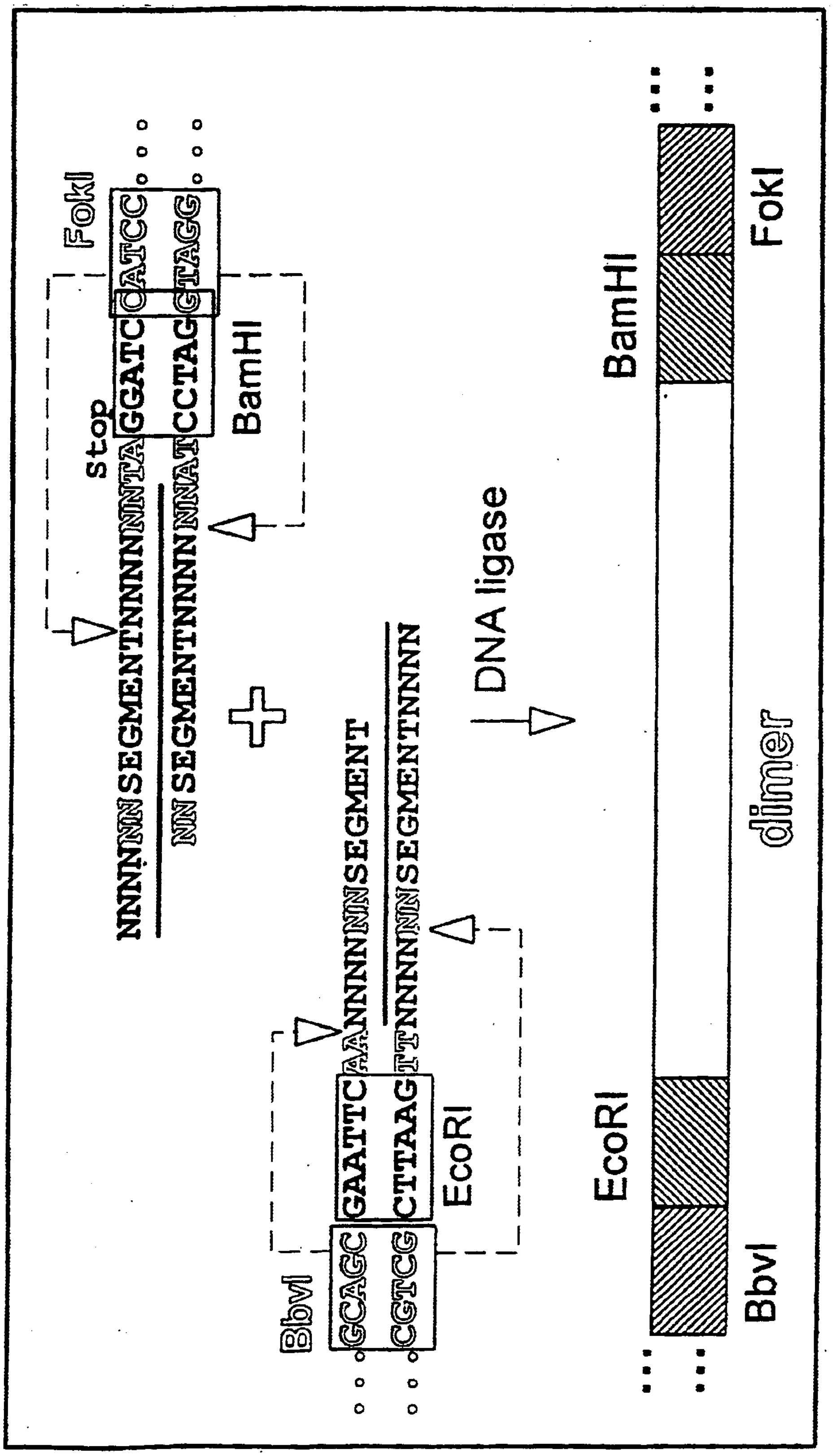
FIG. 8 demonstrates the ligation of a FokI treated first monomer with a BbvI treated second monomer with DNA ligase to create a dimer.

The method further comprises the step of ligating the initial oligonucleotide and the subsequent oligonucleotide together at the downstream initial ligating sequence of the initial oligonucleotide and the upstream subsequent ligating sequence of the subsequent oligonucleotide to form an artificial gene. An example of this step is shown in FIG. 8. The invention contemplated that additional subsequent oligonucleotides can be prepared, cleaved and ligated in a likewise fashion to make any artificial gene.

In a preferred embodiment, the invention provides the subsequent step of cleaving the artificial gene with the first and third endonucleases and inserting the remaining artificial gene into a vector previously cleaved with the first and third endonucleases. This step permits insertion of the final vector construct into a living organism, such as *E. coli*, and the recombinant expression of the artificial gene to produce the mosaic protein.

Figure 5:
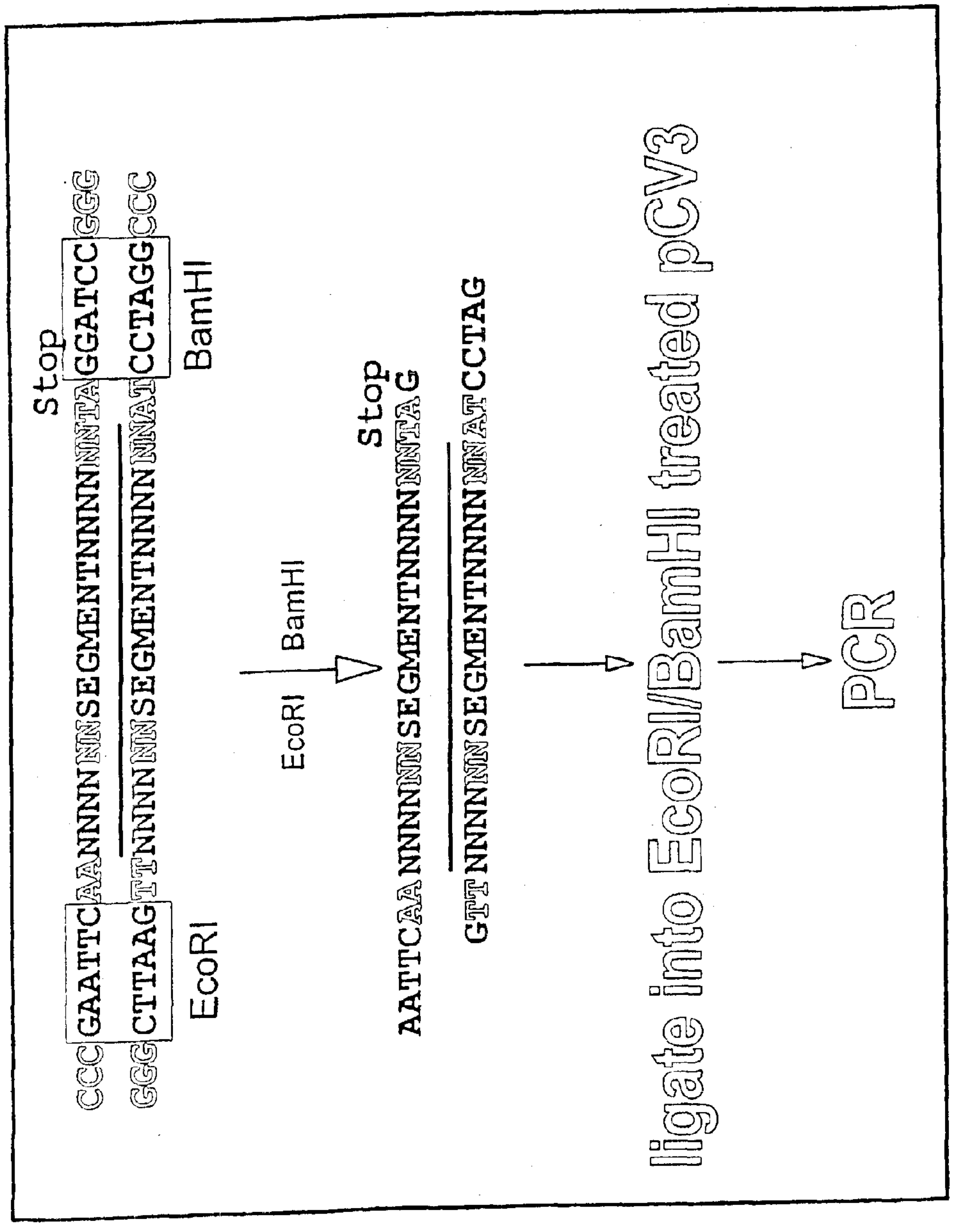
FIG. 5 depicts the cloning strategy of each monomer. The fragments were treated with EcoRI and BamHI followed by ligation into similarly treated pCV3.

The invention provides the unique opportunity following the synthesizing the initial oligonucleotide step, and before the cleaving the initial oligonucleotide with the fourth endonuclease step, of confirming the operability of the initial oligonucleotide by cleaving the initial oligonucleotide with the first and third endonucleases and inserting the remaining initial oligonucleotide into a vector previously cleaved with the first and third endonucleases, and expressing the initial gene segment. An example of such an additional step is shown in FIG. 5, wherein "SEGMENT" designates the initial gene segment and "NNNNNN" designates the initial ligating sequence. This step is made possible by the inclusion of the stop codon downstream of the gene segment, which is removed by the addition of the fourth endonuclease in subsequent steps.

In preferred embodiments, the first and third endonucleases are EcoRI and BamHI, respectively. However, it will be understood that any endonucleases that cleave at the recognition sequence, can be used, with the proviso that two different endonucleases are employed. Examples of other suitable restriction endonucleases include: AflII, Alw44I, ApaI, ApaII, BclI, BglII, BspHI, BssHII, HindIII, KpnI, MluI, NarI, NcoI, PstI, SalI, or XhoI.

In preferred embodiments, the second and fourth endonucleases are BbvI and FokI, respectively. However, it will be understood that any endonuclease that cleaves downstream of the first endonuclease recognition sequence, or upstream of the third endonuclease recognition sequence, respectively, and within the ligating sequences, can be used, with the proviso that two different endonucleases are employed. Examples of other suitable restriction endonucleases that restrict the nucleic acid at a site away from the recognition site include: BspMI, HgaI, MboII, or SfaNI.

The invention provides that in preferred embodiments the initial and subsequent gene segments encode antigenic regions of a homologous protein from different genotypes of a hepatitis virus. The invention contemplates, however, that the REAL technique can be used for the construction of any mosaic or chimeric protein. In preferred embodiments, the gene segments encode antigenic regions of homologous proteins of different genotypes of a hepatitis C virus. Preferably, the gene segments encode antigenic regions of a nucleocapsid protein or a non-structural protein of different genotypes of a hepatitis C virus.

The invention further provides an artificial gene constructed by the above methods. The invention further provides a mosaic protein encoded by the artificial gene constructed by the above methods. The invention further provides a method of detecting a hepatitis infection in an individual comprising combining a serum sample from the individual with the mosaic protein made by the above methods, and detecting the presence of antibody binding to the mosaic protein, the presence of binding indicating a hepatitis infection in the individual. Preferably, an enzyme immunoassay (EIA) is performed for detection of a hepatitis infection, as is described in Examples 2 and 3. The detection of antibody binding can be facilitated by the use of detectable moieties, such as fluorescence, radioisotopes or solid substrate capture.

The invention provides mosaic proteins comprising a plurality of homologous antigenic peptides from different genotypes of a hepatitis virus. In particular, the invention provides mosaic proteins comprising a plurality of homologous antigenic nucleocapsid peptides from different genotypes of a hepatitis C virus. Further, the invention provides mosaic proteins comprising a plurality of homologous antigenic non-structural peptides from different genotypes of a hepatitis C virus. The invention also provides the gene sequences which encode for such mosaic proteins.

In one preferred embodiment, the mosaic protein can comprise a plurality of homologous antigenic nucleocapsid peptides from different genotypes of a hepatitis C virus as set forth in the amino acid sequences set forth in SEQ ID NOs:23–33, detailed in Example 2, herein. In another preferred embodiment, the mosaic protein can comprise a plurality of homologous antigenic non-structural peptides from different genotypes of a hepatitis C virus as set forth in the amino acid sequence of SEQ ID NO:52, detailed in Example 3, herein. It will be understood that certain minor or silent amino acid modifications and/or substitutions can be made in the amino acid sequences, while maintaining the antigenic functionality of the mosaic proteins. It will also be understood that certain silent or wobble nucleotide modifications and/or substitutions can be made in the gene sequences, while maintaining the ability of the gene to be ligated by the REAL technique and the antigenic functionality of the encoded mosaic proteins.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims. The references mentioned in this specification are hereby incorporated by reference in their entireties.

EXAMPLE 1

Restriction Endonuclease Assisted Ligation

Each monomer, or DNA segment encoding a peptide of interest, was prepared from synthetic oligonucleotides of 40–80 nucleotides that overlapped at 8–10 nucleotides and contained an EcoRI site on the 5'-terminus of the plus strand and a BamHI site on the 5'-terminus of the negative strand. More detailed examples of such monomers can be seen in SEQ ID NOs:1–22 and 34–51 described in Examples 2 and 3 herein. Single strand DNA was converted to double stranded DNA by adding 50 pmol of each oligodeoxynucleotide, 2 $\mu$l BamHI buffer (Boehringer Mannheim, Indianapolis, Ind.) and 2.5 pmol dNTPs in a total volume of 20 $\mu$l. The mixture was heated to 95° C. for 1 minute and cooled on ice. After adding 1 $\mu$l of the Klenow fragment of DNA polymerase I (Promega, Madison, Wis.), the reaction mixture was incubated 30 minutes at room temperature. An incubation step at 65° C. for 10 minutes was used to inactivate the DNA polymerase. The resulting double stranded DNA molecule was cleaved with the restriction enzymes EcoRI and BamHI and ligated into pCV3 using the T4 DNA fast ligation kit (Boehringer Mannheim, Indianapolis, Ind.). (FIG. 1) All internal BbvI, EcoRI, BamHI, and FokI restriction endonuclease sites were previously removed from the synthetic gene by introducing synonymous modifications into codons.

Figure 2:
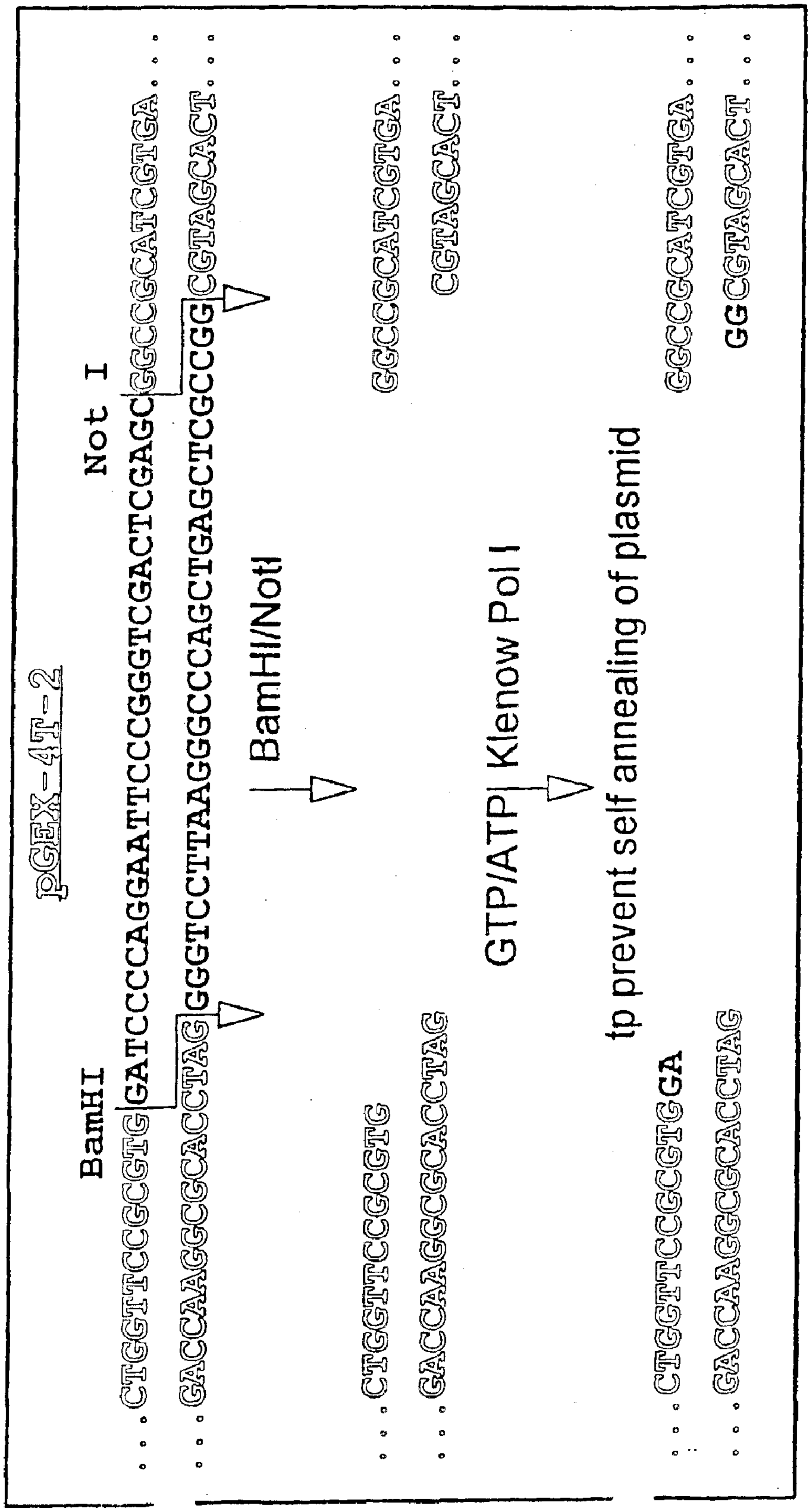
FIG. 2 is a schematic representation of the pCV3 vector design, and demonstrates that the pGEX-4T-2 vector (SEQ ID NO:53) was treated with BamHI and NotI to remove the multiple cloning site. The recovered cleaved vector was then treated with Klenow fragment of DNA polymerase I in the presence of GTP and ATP to prevent self annealing of plasmid.
Figure 3:
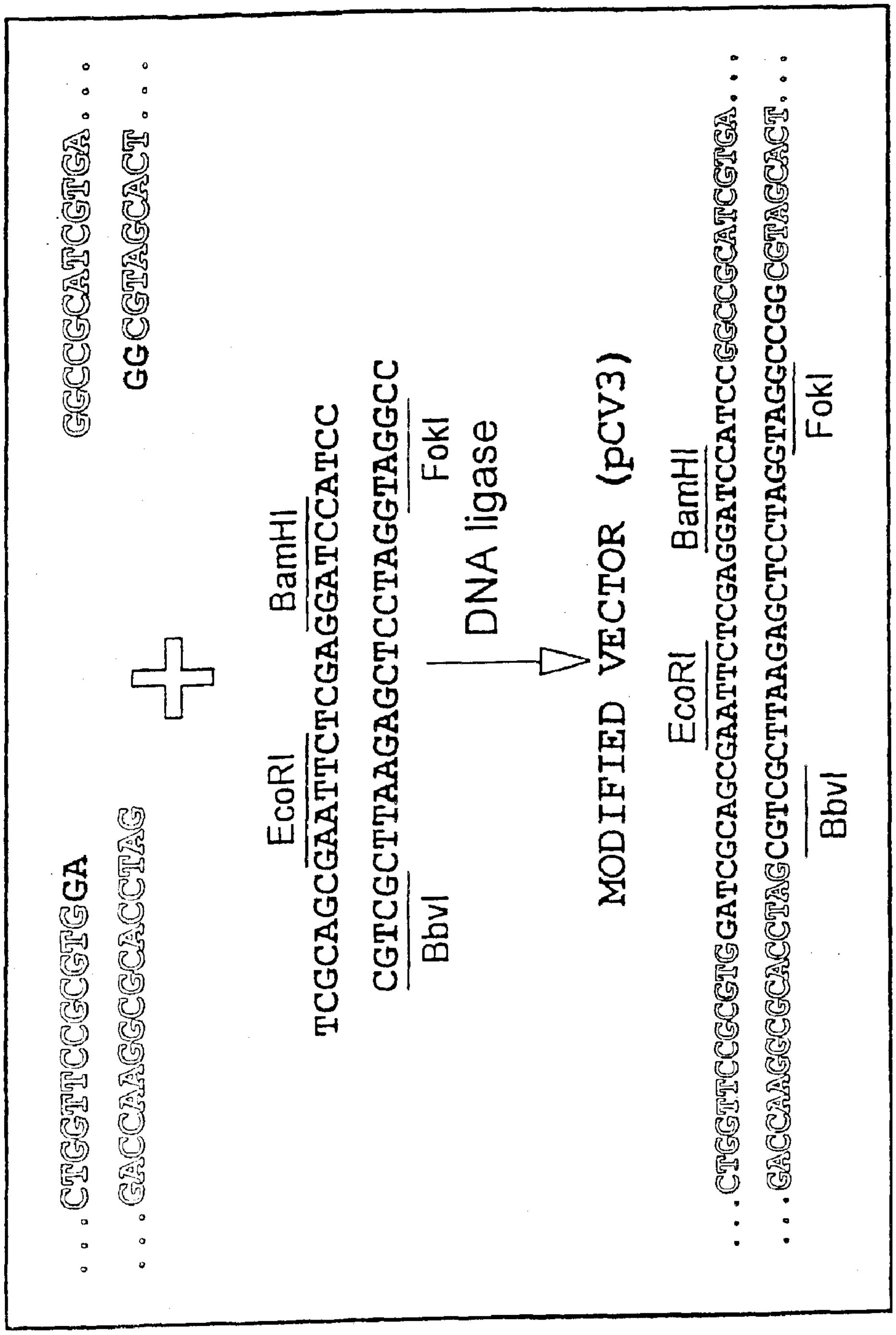
FIG. 3 shows the ligation of a new multiple cloning site sequence (SEQ ID NO:54) into cloning vector by DNA ligase to create the vector pCV3 (SEQ ID NO:55).

The pCV3 vector was created by modification of the multiple cloning site in the expression vector pGEX-4T-2 (Pharmacia, Piscataway, N.J.). After cleaving the vector with BamHI and NotI to remove the internal EcoRI site, the recovered vector was treated with the Klenow fragment of DNA polymerase (Promega, Madison, Wis.) in the presence of GTP and ATP to prevent self annealing of the restricted plasmid. (FIG. 2) Subsequently, a double-stranded DNA molecule was prepared by annealing two complimentary oligonucleotides containing one EcoRI site flanked by a BbvI site, and one BamHI site flanked by a FokI site. This DNA molecule was inserted into the multiple cloning site of the modified vector by DNA ligase. (FIG. 3) The final structure of pCV3 was confirmed by restriction enzyme analysis and by DNA sequencing.

Figure 4:
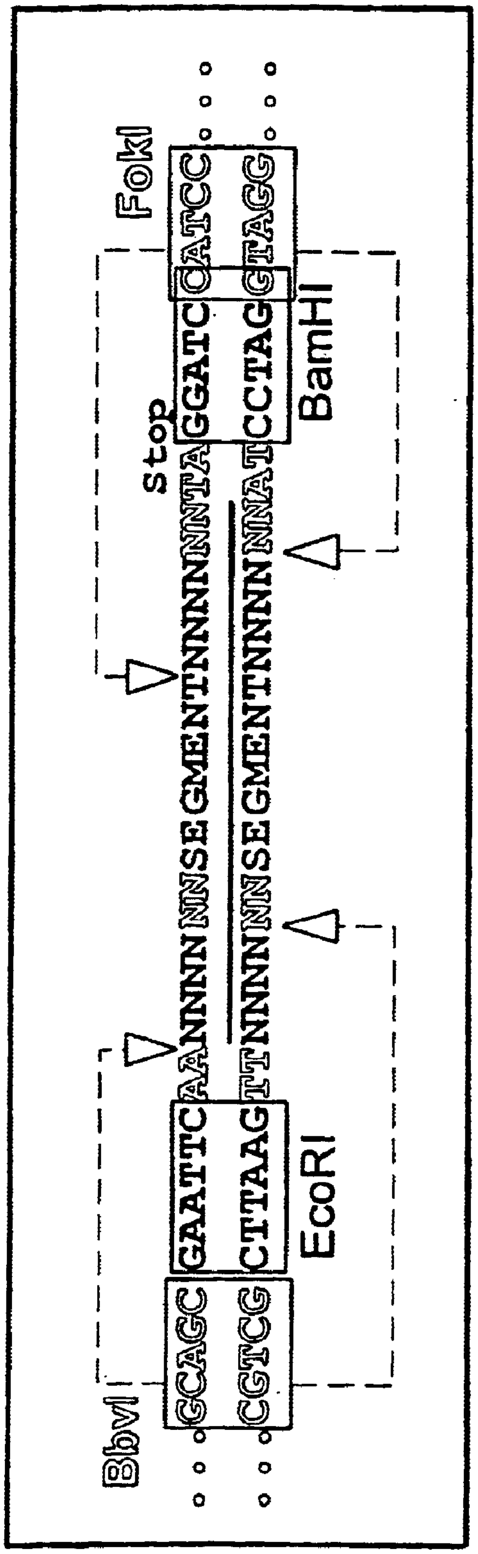
FIG. 4 is a schematic representation of the design of the cloned segment. The bar represents a specific immunoreactive epitope from an appropriate etiologic agent.

After each monomer was inserted into the pCV3 vector, it was amplified by PCR using plasmid specific primers thereby acquiring BbvI and FokI sites and each structure was confirmed by restriction endonuclease analysis and DNA sequencing. FIG. 4 shows the elements for each cloned monomer or segment of the synthetic gene. The solid line separating each strand represents the coding sequence of each monomer followed by a stop codon so that each fragment may be individually expressed. The EcoRI and BamHI sites are used for cloning, while the BbvI and FokI sites are used to remove the EcoRI and BamHI sites and to produce overhangs complimentary to the next consecutive monomer.

The process of consecutive assembly of monomers or fragments into a synthetic gene is illustrated in FIGS. 5–8. The first monomer is restricted with EcoRI and BamHI and ligated into similarly treated pCV3. Following amplification by PCR each segment acquired the restriction sites BbvI and FokI (FIG. 4). Restriction with BbvI creates a 5' overhang 8 base pairs downstream of a GCAGC sequence, whereas restriction with FokI creates a 5' overhang 9 base pairs downstream of a GGATG sequence. Therefore, upon reversing the order of the FokI site on the anti-sense strand of the DNA to create a 3' overhang, and situating the restriction sites 8 and 9 base pairs, respectively, from 4-nucleotide complimentary sequences, each consecutive monomer was alternately treated with FokI and BbvI to produce complimentary overhangs, a 3'-overhang on the first segment and a 5'-overhang on the second segment (FIGS. 6 and 7). The restricted segments were separated by agarose gel electrophoresis using 25% low melting point agarose and stained with ethidium bromide. After staining with ethidium bromide and cutting out the bands with correct size, the DNA was extracted by using the Wizard PCR preps (Promega, Madison, Wis.) following the instructions of the manufacturer. Bands corresponding to the restricted segments were recovered by melting the agarose, and each segment was purified using the Wizard PCR Preps DNA Purification System (Promega, Madison, Wis.).

Subsequently, the first amplified segment was treated with FokI to produce a 5'-overhang complimentary to the 3'-overhang on the second monomer created by treatment with BbvI. Each of the treated segments were purified and ligated with DNA ligase. When two monomers were treated as described above, a dimer was formed which could be subsequently treated with EcoRI and BamHI, and cloned into similarly treated pCV3. Since each segment was supplied with its own stop codon, each monomer, dimer, and multimer could be expressed and analyzed individually.

EXAMPLE 2

Design and Production of an Artificial Nucleocapsid Mosaic Protein

Analysis of Data Derived from Genebank

The N-terminal region spanning amino acids 5–33 of the nucleocapsid (NC) protein was selected as the region to develop a mosaic protein because of the presence of several strong and broadly immunoreactive antigenic epitopes (unpublished data). All known HCV sequences deposited in Genebank were analyzed using the program FASTA (Wisconsin Package 9.0, Genetics Computer Group (GCG), Madison, Wis.). Out of 77 available sequences demonstrating variations in this region, 11 variants representing 3 different HCV genotypes were selected for designing an artificial mosaic gene. FIG. 9 represents the amino acid sequence of each of the 11 variants, referred to as fragments or monomers, comprising the mosaic NC protein.

Synthetic Gene Assembly

The construction of the artificial gene was accomplished using the previously described Restriction Endonuclease Assisted Ligation (REAL) method and the following synthetic oligonucleotides:

```
A1: 5'-CCC CGA ATT CAA CCG AAA CCG CAA CGT AAA    (SEQ ID NO:1);
ACC AAA CGT AAC ACC ATT CGT CGT C

A2: 5'-CCC CGG ATC CTA TTT CGG ACC AAC GAT CTG    (SEQ ID NO:2);
ACC ACC ACC CGG GAA TTT AAC GTC CTG CGG ACG
ACG AAT

B1: 5'-CCC CGA ATT CAA CCG AAA CCG CAA CGT CAG    (SEQ ID NO:3);
ACC AAA CGT AAC ACC AAC CGT CGT

B2: 5'-CCC CGG ATC CTA TTT CGG ACC AAC GAT CTG    (SEQ ID NO:4);
ACC ACC ACC CGG GAA TTT AAC GTC CTG CGG ACG
ACG GTT G

C1: 5'-CCC CGA ATT CAA CCG AAA CCG CAA CGT AAA    (SEQ ID NO:5);
ACC AAA CGT AAC ACC TAC CGT

C2: 5'-CCC CGG ATC CTA TTT CGG ACC AAC GAT CTG    (SEQ ID NO:6);
ACC ACC ACC CGG GAA TTT AAC GTC CTG CGG ACG
ACG GTA GGT G

D1: 5'-CCC CGA ATT CAA CCG AAA CCG CAA CGT AAA    (SEQ ID NO:7);
CCG AAC CGT AAC ACC AAC CGT CGT C

D2: 5'-CCC CGG ATC CTA TTT CGG ACC AAC GAT CTG    (SEQ ID-NO:8);
ACC ACC ACC CGG GAA TTT AAC GTC CTG CGG ACG
ACG GTT

E1: 5'-CCC CGA ATT CAA CCG AAA CCG CAA CGT CAG    (SEQ ID NO:9);
CCG AAA CGT AAC ACC CCG CGT CGT CCG CAG GAC

E2: 5'-CCC CGG ATC CTA TTT CGG ACC AAC GAT CTG    (SEQ ID NO:10);
ACC ACC ACC CGG GAA TTT AAC GTC CTG CGG
```

-continued

```
F1: 5'-CCC CGA ATT CAA CCG AAA CCG CAA CGT AAA    (SEQ ID NO:11);
ACC AAA CGT AAC GCT CAC CGT CGT C

F2: 5'-CCC CGG ATC CTA TTT CGG ACC AAC GAT CTG    (SEQ ID NO:12);
ACC ACC ACC CGG GAA TTT AAC GTC CTG CGG ACG
ACG GTG

G1: 5'-CCC CGA ATT CAA CCG AAA CCG CAA CGT AAA    (SEQ ID NO:13);
AAC CAG CGT AAC ACC AAC CGT CGT C

G2: 5'-CCC CGG ATC CTA TTT CGG ACC AAC GAT CTG    (SEQ ID NO:14);
ACC ACC ACC CGG GAA TTT AAC GTC CTG CGG ACG
ACG GTT

H1: 5'-CCC CGA ATT CAA CCG AAA CCG CAA CGT AAA    (SEQ ID NO:15);
ACC AAA CGT AAC ACC ATt CGT CGT C

H2: 5'-CCC CGG ATC CTA TTT CGG AAC GTA GAT AAC    (SEQ ID NO:16);
ACC ACC ACC CGG GAA TTT AAC GTC CTG CGG ACG
ACG AAT

I1: 5'-CCC CGA ATT CAA CCG AAA CCG CAA CGT AAA    (SEQ ID NO:17);
ACC GAA CGT AAC ACC AAC CGT CGT CC

I2: 5'-CCC CGG ATC CTA TTT CGG ACC AAC GAT CTG    (SEQ ID NO:18)
ACC ACC ACC AGA GAA ACG AAC GTC CGG ACG ACG GT

J1: 5'-CCC CGA ATT CAA CCG AAA CCG AAA CGT CAG    (SEQ ID NO:19);
ACC AAA CGT AAC ACC CTG CGT CGT

J2: 5'-CCC CGG ATC CTA TTT CGG ACC AAC GAT CTG    (SEQ ID NO:20);
ACC ACC AGC CGG GAA TTT AAC GTT TTT CGG ACG
ACG ACG CAG G

K1: 5'-CCC CGA ATT CAA CCG AAA CCG CAA CGT AAA    (SEQ ID NO:21);
ACC AAA CGT AAA GCT CAC CGT CGT C

K2: 5'-CCC CGG ATC CTA TTT CGG ACC AAC GAT CTG    (SEQ ID NO:22).
ACC ACC ACC CGG GAA TTT AAC GTC CTG CGG ACG
ACG GTG
```

Figure 10:
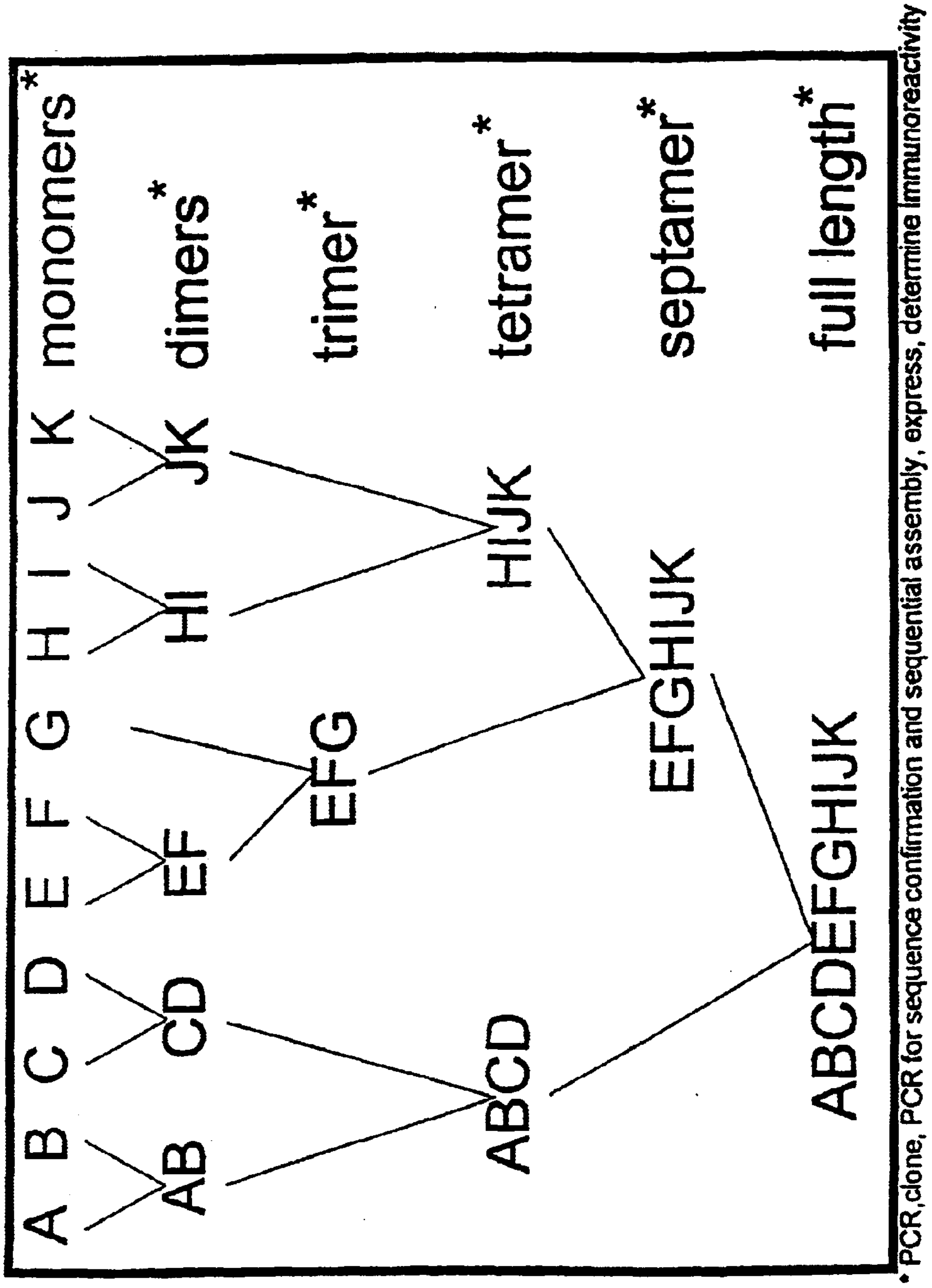
FIG. 10 depicts the strategy of assembly from individual NC monomers by REAL resulting in a full length gene composed of monomers ABCDEFGHIJK. The primary sequence of all cloned fragments were confirmed prior to assembly by REAL.

Each pair of oligonucleotides was converted into double stranded DNA by the Klenow fragment of DNA Polymerase I and subsequently cloned, resulting in 11 monomers of 28 amino acids. Prior to sequential assembly by REAL, each fragment was amplified by the polymerase chain reaction, and determined to be the expected molecular weight by agarose gel electrophoresis with ethidium bromide staining. Additionally, the primary structure of each fragment was confirmed by sequencing. To begin assembly of the mosaic protein, two consecutive monomers were assembled into 5 dimers as shown in FIG. 10. In the next step, the remaining monomer, G, was fused with the dimer EF to form a trimer, while the other consecutive dimers were assembled into the tetramers ABCD and HIJK. Fragments EFG and HIJK were then assembled into a septamer, and the septamer was assembled into a full length, 924 base pair gene by adding the tetramer ABCD.

Protein Expression and Purification

Proteins were fused to the C-terminus of glutathione S-transferase by transforming competent *Escherichia coli* cells, JM 109 (Invitrogen, San Diego, Calif.), with plasmids containing each of the fragments. Cells were grown in LB medium containing 100 $\mu$g Ampicillin per ml in a bacteria shaker at 37° C. until the optical density at 600 nm was equal to 0.6. The tac promoter was activated to achieve protein expression by adding isopropyl-b-D-thiogalactoside (IPTG) at a final concentration of 1 mM. After 1 hour growth at 30° C., the cells were harvested, and a lysate was prepared following the procedure described by Sambrook J., et al., in *Molecular Cloning—A Laboratory manual*, latest edition, p. 17.38, Cold Spring Harbor Laboratory Press, New York, 1989. The glutathione S-transferase-mosaic fusion proteins were then purified by affinity chromatography using glutathione-Sepharose columns (Pharmacia, Piscataway, N.J.) (Smith D. B. and Johnson K. S., Gene 67:37–40, 1988).

Analysis of NC Expressed Fragments

*E. coli* cells were transformed with plasmid constructs containing each of the PCR amplified fragments. After induction with IPTG, crude lysates were prepared and high yields of proteins of the expected molecular mass were observed after analysis by 12% SDS-PAGE (data not shown). A comparison of different induction conditions indicated that induction with 1 mM IPTG for 1 hour at 30° C. gave the highest yield of soluble mosaic-fusion proteins (data not shown). Following the preparation of lysates, the proportion of soluble protein was estimated to be about 50–60%. Each expressed NC fragment was purified by affinity chromatography according to the manufacturer's recommendations, and analyzed by 12% SDS-PAGE and Coomassie blue staining. All 21 purified proteins demonstrated a high degree of purity and electrophoresed to their expected molecular weights. Although an artifactual doublet was present in many of the samples, this result is typical of the glutathione S-transferase (GST) expression system. The full length NC mosaic protein electrophoresed as a single band with an estimated molecular weight of 61 kDa.

Immunoblot Assay

Figure 11:
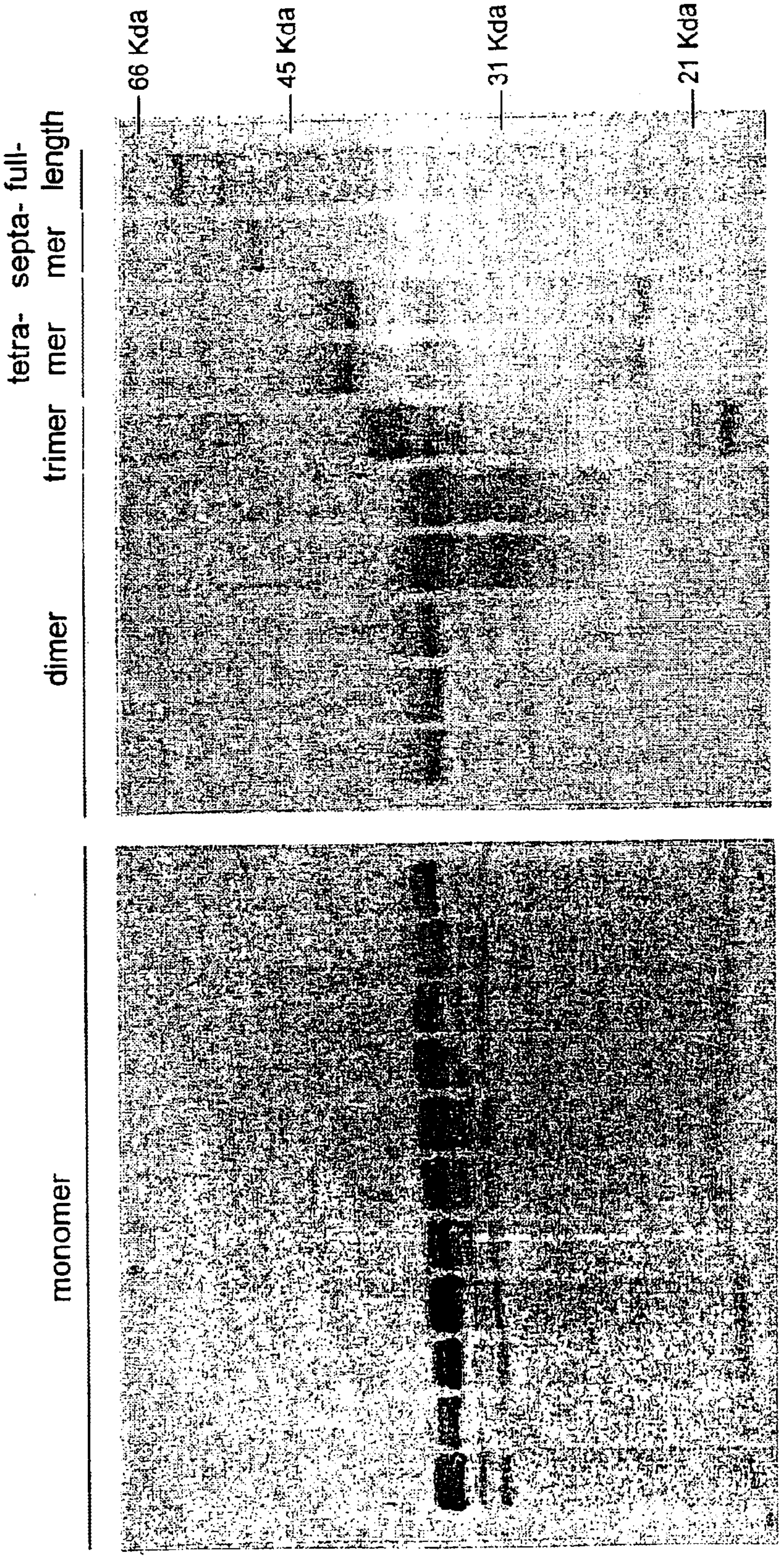
FIG. 11 shows the analysis of selected expressed and purified protein by immunoblot analysis. A single anti-HCV positive human sera with high anti-NC activity by MATRIX immunoassay was used as the source of primary antibody.

To verify the immunoreactivity of each fragment, the GST-mosaic fusion proteins were analyzed by immunoblot using an anti-HCV positive sample having high anti-NC activity by MATRIX immunoassay. Nitrocellulose membranes containing immobilized proteins were incubated for 1 hour with anti-NC positive human sera diluted 1:200 times in washing solution (0.1M PBS, pH 7.2, containing 1% BSA, and 0.5% Tween 20). The membranes were washed three times with washing solution and then incubated for 1 hour with affinity-purified goat anti-human immunoglobulin G conjugated to horseradish peroxidase (Biorad, Richmond, Calif.) diluted 1:5000 in washing solution. After washing, diaminobenzidine and hydrogen peroxide were added to develop the color reaction. As shown in FIG. 11 (asterisks indicate the location of specific immunoreactivity), each of the purified proteins demonstrated immunoreactivity suggesting the accessibility of immunoreactive epitopes. The monomers were the least immunoreactive, and as the fragments increased in size they became increasingly more immunoreactive. Many of the lanes corresponding to the higher molecular weight fragments demonstrate specific reactivity to proteolytic cleavage products. Although FIG. 11 shows data for 16 of the 21 proteins, the remaining 5 proteins behaved in a similar manner.

NC Mosaic EIA

Twenty nanograms of full length affinity-purified GST-mosaic NC fusion protein in PBS (pH 7.5) was added to microtiter wells (Immunolon II: Dynatech Laboratories, Inc., Chantilly, Va.) and allowed to adsorb at room temperature for 12 hours after which the wells were blocked with 10% normal goat serum (NGS), and 1% BSA in PBS for 2 hours at 37° C. Human sera diluted 1:500 in 0.1 M phosphate-buffered saline, pH 7.5, containing 0.1% Tween 20 and 10% NGS was added and incubated for 1 hour at 37° C. After washing, goat anti-human IgG conjugated to horseradish peroxidase diluted 1:5000 in 0.1 M PBS, pH 7.5, containing 0.1% Tween 20 and 10% NGS was added, and the wells were incubated for 1 hour at 37° C. The wells were incubated for ten minutes in the dark with substrate. Acid was added to stop the reaction and optical density (OD) was measured at 490 nm.

Serum Samples

Several collections of specimens were used to characterize the various fragments and to assess the NC Mosaic EIA: 1.) 128 anti-HCV positive specimens obtained from paid plasma donors (Boston Biomedica Inc., West Bridgewater, Mass.), 2.) a collection of normal blood donors negative for anti-HCV activity reposited at CDC, 3.) 21 anti-HCV positive and genotyped specimens (Boehringer Mannheim, Mannheim, Germany), and 4.) 4 anti-HCV positive seroconversion panels (Serologicals Inc., Clarkston, Ga.).

NC Mosaic EIA Results

Figure 12:
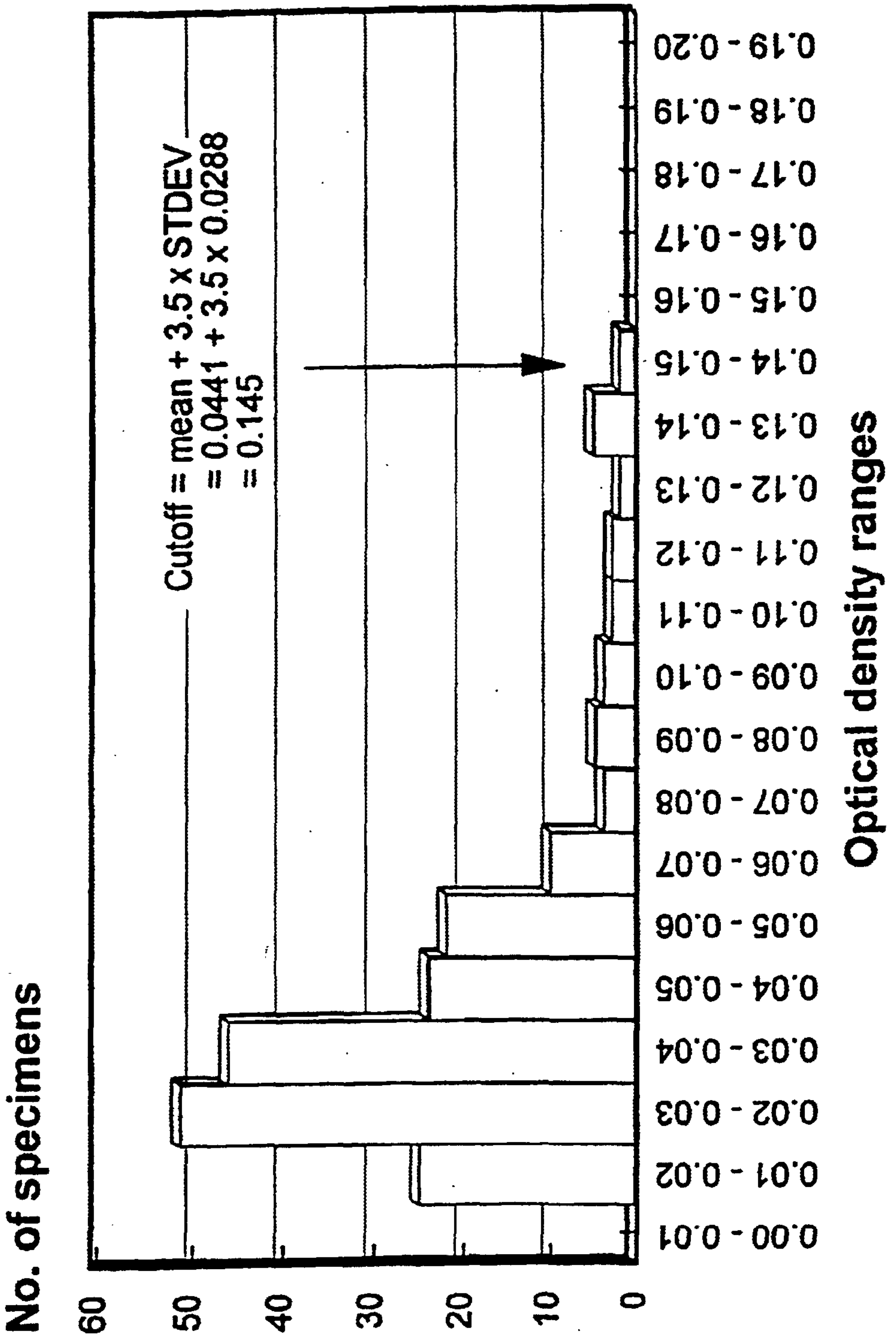
FIG. 12 shows the frequency distribution of 200 anti-HCV negative sera by NC Mosaic EIA for the detection of anti-NC activity. The cutoff value was statistically derived as the mean optical density (OD) value of negative sera plus 3.5 times the standard deviation of the mean. This value equals 0.145.

A frequency distribution of 200 anti-HCV negative specimens were tested by EIA to statistically derive a cutoff value (FIG. 12). This value was set at an OD value greater than the mean OD plus 3.5 standard deviations of the mean or 0.145. When applying this cutoff value one of the anti-HCV negative specimens gave an OD value equal to 0.145, which was interpreted as negative, giving an overall specificity of 100%.

Figure 13:
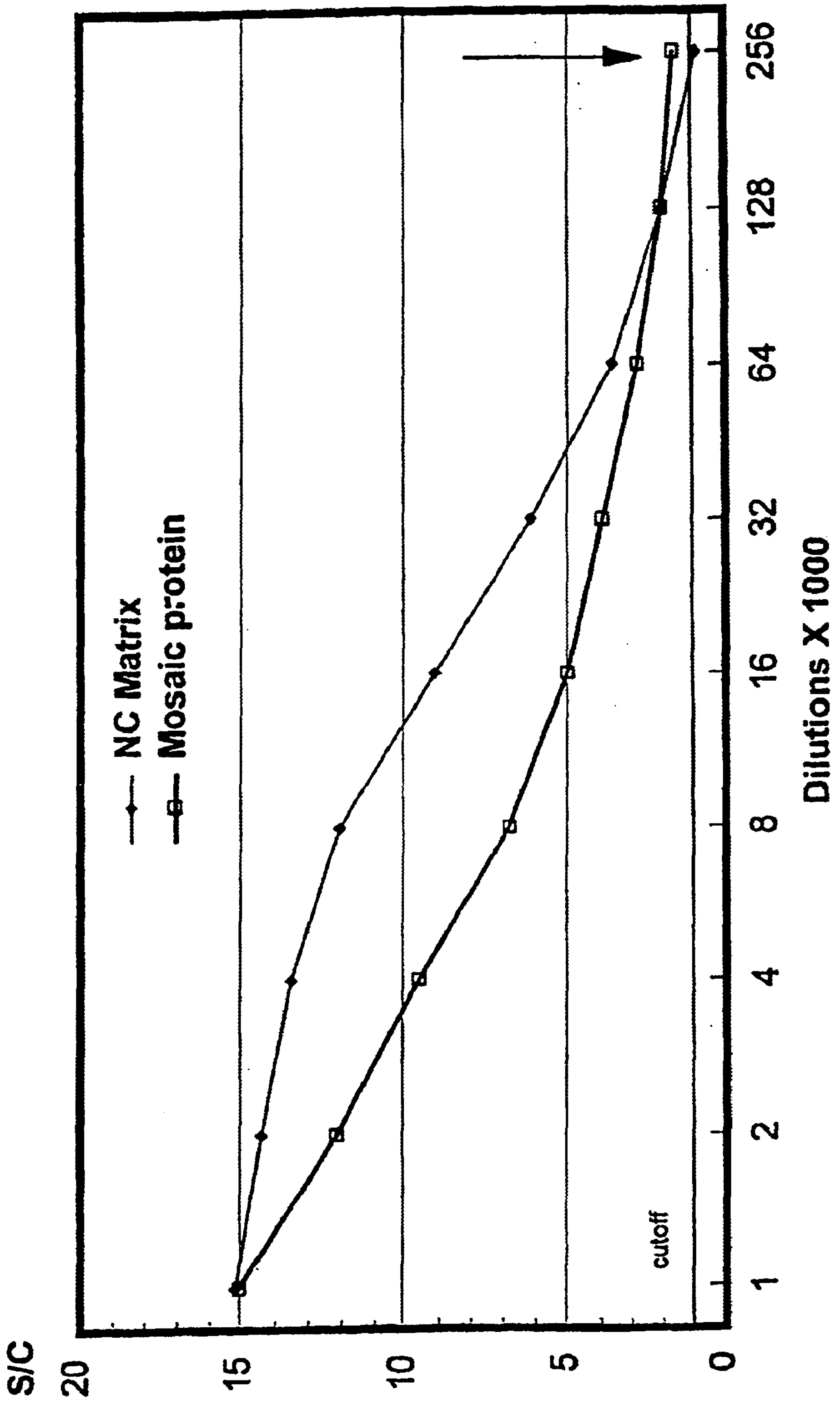
FIG. 13 shows an endpoint titration of specimen no. BBI 304 by NC Mosaic EIA and by MATRIX immunoassay for the detection of anti-NC activity.
Figure 14:
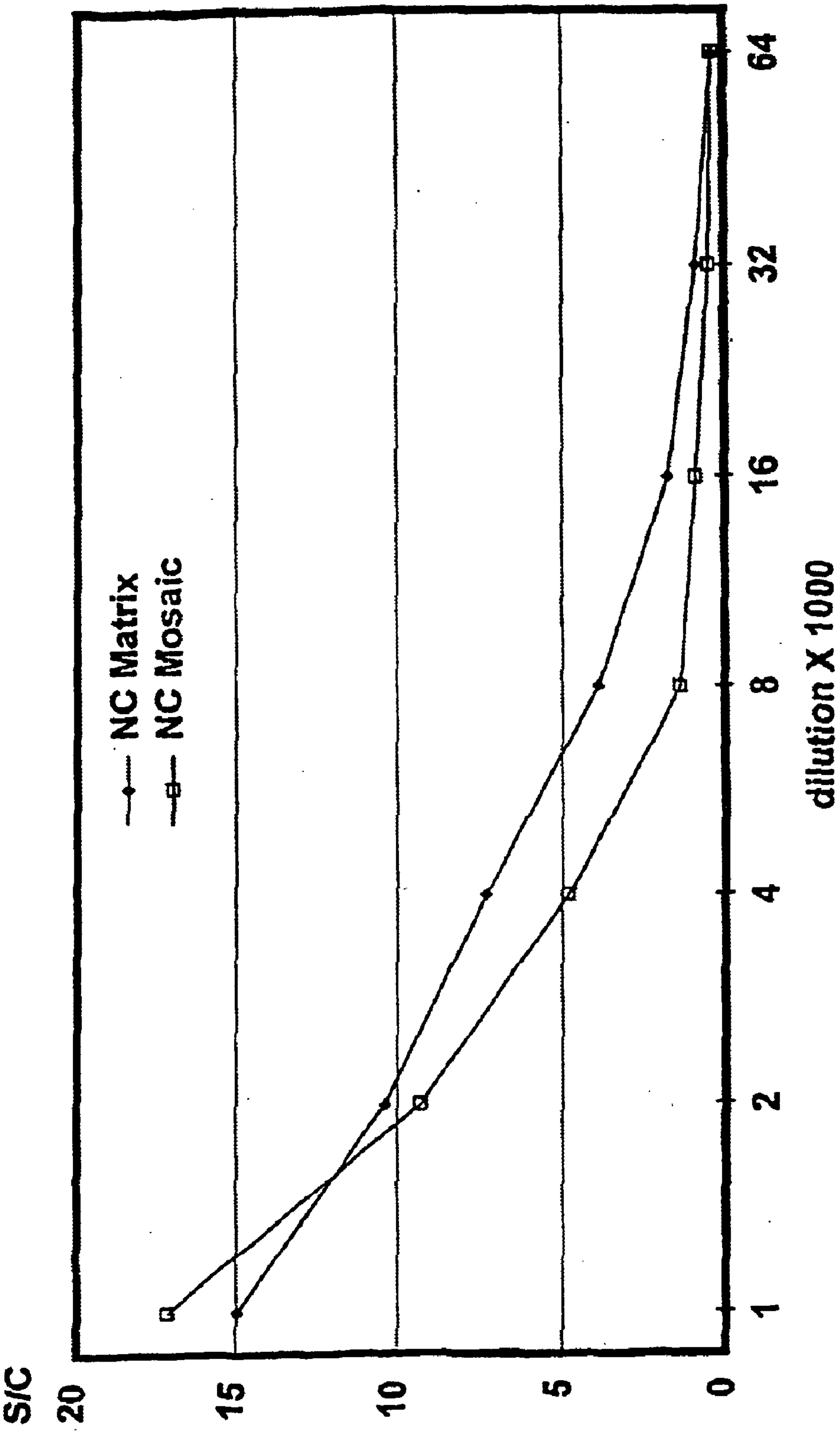
FIG. 14 shows an endpoint titration of specimen no. BB1325 by NC Mosaic EIA and by MATRIX immunoassay for the detection of anti-NC activity.

Two serially diluted specimens, BBI 304 and BBI 325 were tested by the NC Mosaic EIA and by MATRIX immunoassay to determine relative sensitivities. The results were expressed as sample to cutoff values (S/CO) so that each test may be directly compared (FIGS. 13 and 14, respectively). A S/CO value greater than 1 is considered positive. Specimen BBI 325 reached an endpoint by MATRIX immunoassay at a dilution of 1:256,000. NC Mosaic EIA gave a S/CO value of 1.8 at that dilution; however, an examination of cutoff values at a 1:64,000 dilution and at a 1:128,000 dilution suggests that the S/CO value for the EIA may not be accurate and that the true endpoint by NC Mosaic EIA may be at a dilution of 1:32,000 or 4-fold less sensitive than MATRIX immunoassay. Conversely, Specimen BBI 304 gave an endpoint titer of 1:128,000 by MATRIX immunoassay, while the NC Mosaic EIA was still positive at a dilution of 1:256,000 suggesting that the EIA was 2-fold more sensitive than MATRIX immunoassay. It is not unusual for several samples to give different endpoint titers since the immunologic targets are very different. The endpoint titers obtained by these two assays on the same sera most probably is a reflection of the relative titers of antibodies to different antigenic epitopes as they are presented within each test format.

Figure 15:
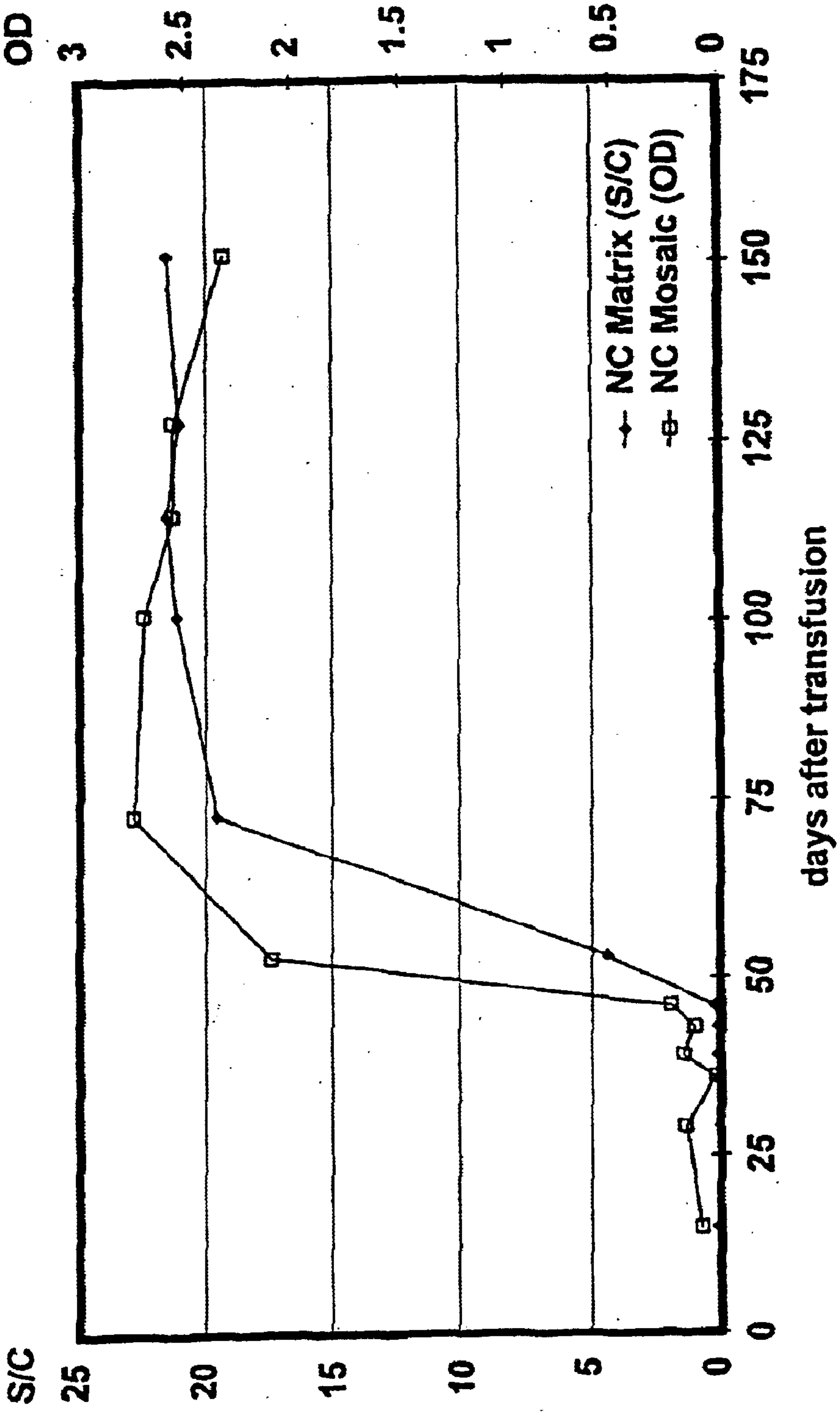
FIG. 15 depicts a comparison of the NC Mosaic EIA (OD y-axis) and MATRIX immunoassay (S/C y-axis) for the detection of anti-NC activity in seroconversion no. 4812.
Figure 16:
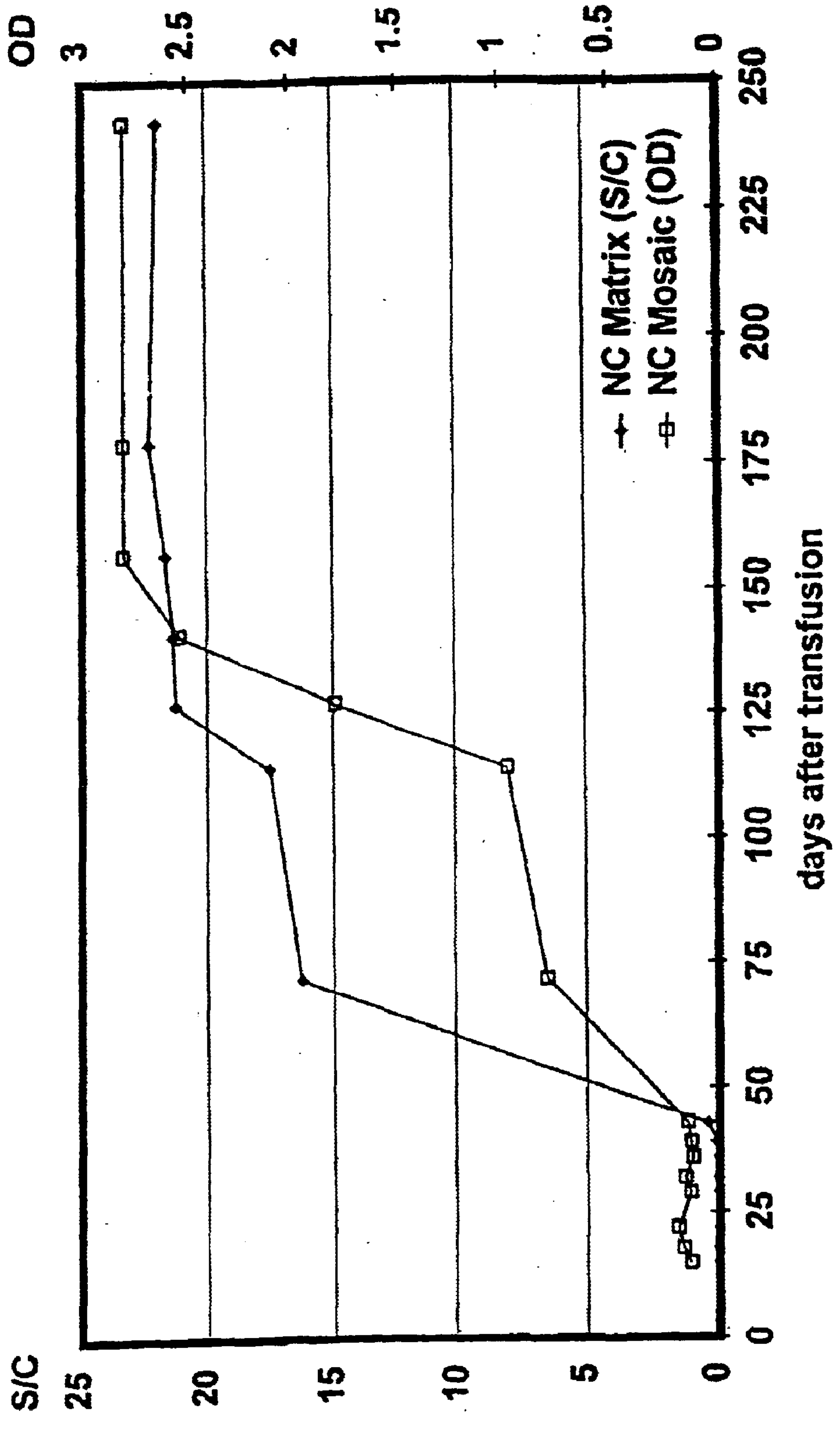
FIG. 16 depicts a comparison of the NC Mosaic EIA (OD y-axis) and MATRIX immunoassay (S/C y-axis) for the detection of anti-NC activity in seroconversion no. 4813.
Figure 17:
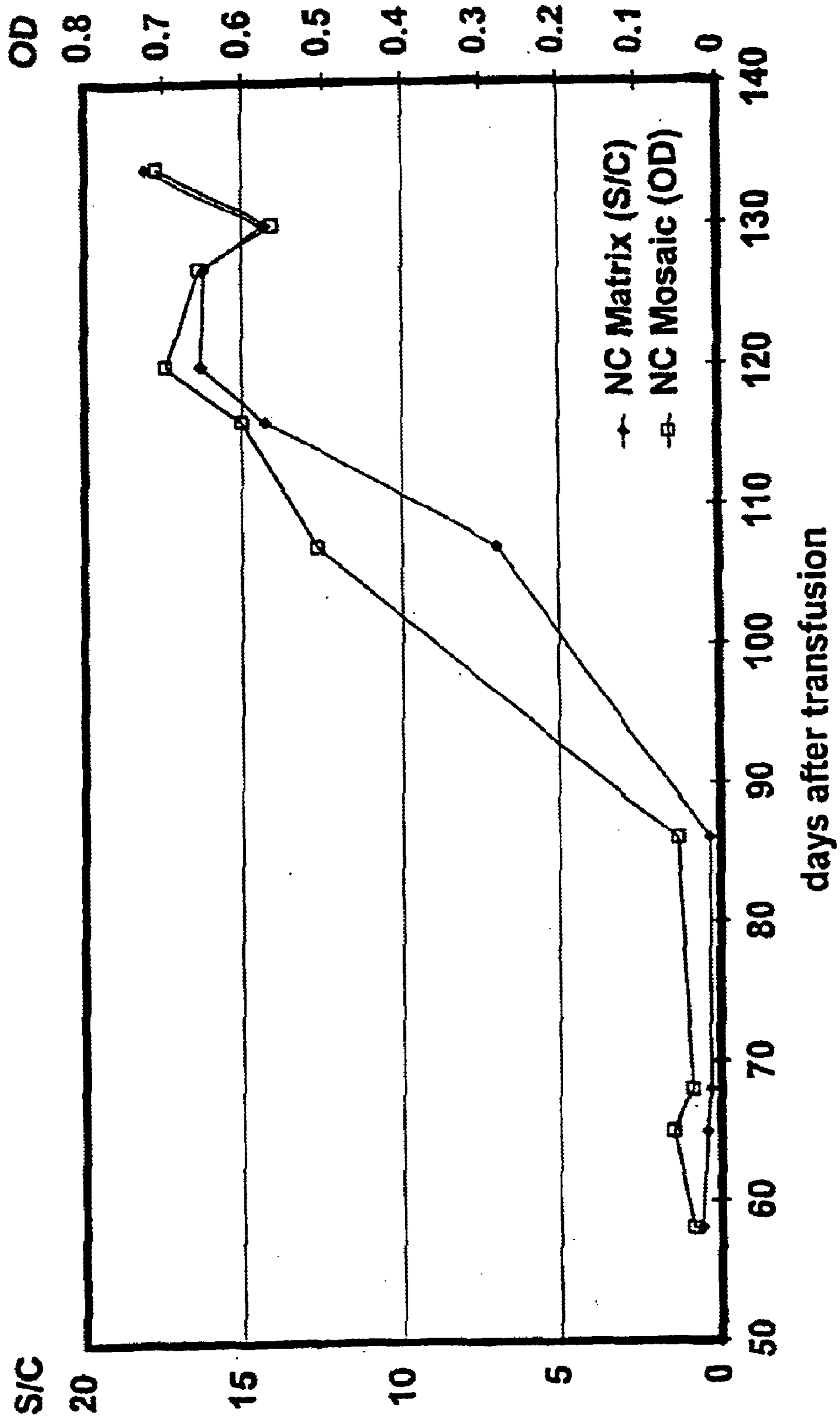
FIG. 17 depicts a comparison of the NC Mosaic EIA (OD y-axis) and MATRIX immunoassay (S/C y-axis) for the detection of anti-NC activity in seroconversion no. 4814.

To measure clinical sensitivity several seroconversion panels (No. 4812, 4813, and 4814) were tested by the NC Mosaic EIA and by MATRIX immunoassay (FIGS. 15, 16, and 17, respectively). A cutoff value of 2.5 times background was used for the NC Mosaic EIA, while a S/CO value greater than 1.0 was used for MATRIX immunoassay. All three seroconversion panels detected anti-NC activity at approximately the same number of days after transfusion.

Another manner to measure clinical sensitivity is to test a panel of anti-HCV positive sera for anti-NC activity by NC Mosaic EIA and by MATRIX immunoassay. A panel of 128 specimens obtained from professional plasma donors tested positive by a commercially available EIA screening assay. Among the 128 initially reactive specimens, 109 were confirmed as positive by MATRIX immunoassay, while 12 tested as indeterminate and 7 as negative. Among the 109 confirmed anti-HCV positive specimens, 101 (92.6%) demonstrated anti-NC activity by MATRIX immunoassay and 99 (90.8%) by NC Mosaic EIA suggesting a slightly higher sensitivity for MATRIX immunoassay. Among the 12 indeterminate specimens, 6 demonstrated anti-NC activity by MATRIX immunoassay, and 3 by NC Mosaic EIA suggesting a higher specificity for the NC Mosaic EIA. None of the 7 anti-HCV negatives were positive for anti-NC activity by either test. (Data not shown).

In another study, among 78 initially reactive specimens 66 were confirmed as anti-HCV positive by MATRIX immunoassay, one specimen tested indeterminate, while 3 tested as negative. The NC Mosaic EIA gave concordant results with MATRIX immunoassay for anti-NC activity for the 66 positive samples and for the one negative specimen. The indeterminate specimen tested negative for anti-NC activity by NC Mosaic EIA suggesting a higher specificity for this specimen. The remaining 8 specimens were known to have nonspecific reactivity to the NS4 antigen, but tested negative by both assays for anti-NC activity. (Data not shown).

Finally, 23 anti-HCV sera representing genotypes 1–5 were tested for anti-NC activity by NC Mosaic EIA and by MATRIX immunoassay. The results indicating a 100% concordance between the two assays (data not shown) indicating that the mosaic NC protein, although composed of sequences from genotypes 1–3, contains crossreacting epitopes that react with anti-NC positive sera obtained from individuals infected with 5 different genotypes. Collectively, these results suggest that the NC mosaic protein when used as the immunologic target in an EIA format is at least as sensitive and possibly more specific than MATRIX immunoassay for the detection of anti-NC activity.

EXAMPLE 3

Design and Production of an Artificial NS4 Mosaic Protein

Design of an Artificial NS4 Mosaic Protein

To construct an artificial NS4 antigen containing antigenic epitopes from several HCV genotypes, all sequences from the 5-1-1 region as well as a strongly immunoreactive region located at the C-terminal of NS4 were searched in GeneBank. Representative regions from different genotypes were selected based upon significant sequence divergence from each other and are shown in FIG. 18.

Gene Assembly

Figure 18:
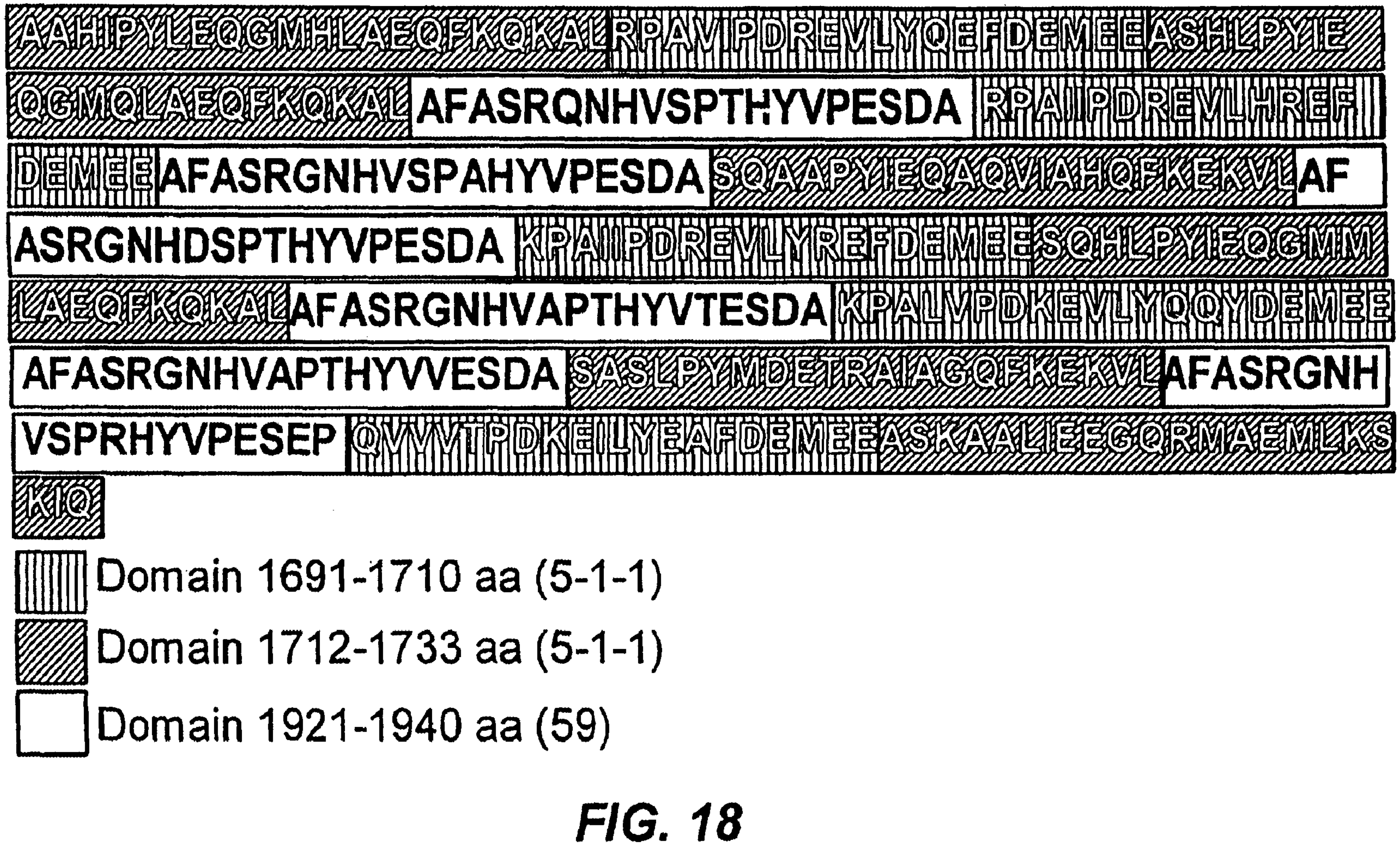
FIG. 18 shows the amino acid sequence of the NS4 mosaic protein. A total of 17 sequences were used corresponding from the same domains from different subtypes and genotypes. Domain 1691–1710 corresponds to the N-terminus of 5-1-1, while domain 1712–1733 corresponds to the C-terminus of 5-1-1. Domain 1921–1940 corresponds to region 59 (C-terminus of NS4).

The amino acid sequence as shown in FIG. 18 was back translated into its nucleotide sequence, and synthetic oligonucleotides, were used to construct nine monomers, the first eight consisting of two antigenic domains and the ninth consisting of one antigenic domain, and were consecutively assembled using Restriction Endonuclease Assisted Ligation (REAL). The synthetic oligonucleotides used were as follows:

```
A1: 5'-CCC CGA ATT CAA GCC GCC CAC ATA CCA TAC    (SEQ ID NO:34);
CTA GAA CAA GGA ATG CAT CTC GCA GAA CAA TTC
AAA CAA AAG GCA CTT CGT C

A2: 5'-CCC CGG ATC CTA ACT AGC CTC TTC CAT CTC    (SEQ ID NO:35);
ATC AAA CTC CTG ATA CAA AAC CTC CCT ATC CGG
GAT AAC AGC CGG ACG AAG TGC

B1: 5'-CCC CGA ATT CAA GCT AGT CAC TTA CCG TAT    (SEQ ID NO:36);
ATC GAG CAG GGA ATG CAG TTA GCT GAA CAG TTT
AAA CAG AAG GCT CTG GCT TTT G

B2: 5'-CCC CGG ATC CTA AGG CCG AGC GTC AGA CTC    (SEQ ID NO:37);
AGG AAC ATA ATG AGT AGG AGA AAC ATG ATT ACC
CCG AGA AGC AAA AGC CAG

C1: 5'-CCC CGA ATT CAA CGG CCT GCG ATA ATA CCG    (SEQ ID NO:38);
GAT AGG GAG GTT CTT CAT AGG GAG TTT GAC GAG
ATG GAG GAG GCT TTT GCG

C2: 5'-CCC CGG ATC CTA CTG CGA AGC ATC AGA CTC    (SEQ ID NO:39);
AGG AAC ATA ATG AGC CGG ACT AAC ATG ATT CCC
ACG AGA CGC AAA AGC C

D1: 5'-CCC CGA ATT CAA TCG CAG GCG GCG CCT TAT    (SEQ ID NO:40);
ATT GAG CAG GCT CAG GTT ATT GCT CAT CAG TTT
AAG GAG AAG GTT CTT GCT TT

D2: 5'-CCC CGG ATC CTA CGG CTT CGC GTC CGA CTC    (SEQ ID NO:41);
AGG AAC ATA ATG AGT CGG AGA ATC ATG ATT ACC
ACG AGA AGC AAA AGC AAG AA

E1: 5'-CCC CGA ATT CAA AAG CCG GCG ATA ATC CCT    (SEQ ID NO:42);
GAC CGT GAG GTT CTG TAT CGT GAG TTT GAT GAG
ATG GAG GAG TCA CAG C

E2: 5'-CCC CGG ATC CTA AAA CGC CAG AGC CTT CTG    (SEQ ID NO:43);
CTT AAA CTG CTC AGC AAG CAT CAT ACC CTG CTC AAT
GTA CGG AAG ATG CTG TGA CTC

F1: 5'-CCC CGA ATT CAA GCG TTT GCT TCT CGT GGT    (SEQ ID NO:44);
AAT CAT GTT GCT CCG ACT CAT TAT GTT ACG GAG
TCA GAT GCT AAG C

F2: 5'-CCC CGG ATC CTA GAA AGC CTC CTC CAT CTC    (SEQ ID NO:45);
ATC ATA CTG CTG ATA AAG AAC CTC CTT ATC CGG
AAC CAG AGC CGG CTT AGC ATC

G1: 5'-CCC CGA ATT CAA GCT TTC GCT TCT CGT GGT    (SEQ ID NO:46);
AAT CAT GTT GCT CCT ACG CAT TAT GTT GTT GAG TCA
GAT GCT TCT GCT TC

G2: 5'-CCC CGG ATC CTA GAA AGC CAG AAC CTT CTC    (SEQ ID NO:47);
CTT AAA CTG ACC AGC AAT AGC ACG CGT CTC GTC
CAT ATA CGG CAG AGA AGC AGA AG

H1: 5'-CCC CGA ATT CAA GCT TTC GCT AGT CGT GGG    (SEQ ID NO:48);
AAT CAT GTG TCG CCG CGT CAT TAT GTG CCT GAG TCT
GAG CCT CAG GTT GT

H2: 5'-CCC CGG ATC CTA AGA AGC CTC CTC CAT CTC    (SEQ ID NO:49);
ATC AAA AGC CTC ATA CAG TAT CTC CTT ATC CGG CGT
AAC AAC AAC CTG AG

I1: 5'-CCC CGA ATT CAA GCT TCT AAG GCC GCG CTG    (SEQ ID NO:50);
ATT GAG GAG GGT CAG CGT ATG G

I2: 5'-CCC CGG ATC CTA CTG GAT CTT AGA CTT CAG    (SEQ ID NO:51);
CAT CTC AGC CAT ACG CTG
```

Gene Expression and Protein Purification

To express the synthetic genes, *E. coli* JM109 competent cells (Promega, Madison, Wis.) were transformed with plasmids containing 9 monomers, 4 dimers, 2 tetramers, and a full size gene using the REAL method described in Example 1. Cells were grown in Luria broth (LB) with 50 mg/ml ampicillin overnight at 37° C. The cultures were then diluted 1:10 in fresh LB with 50 mg/ml ampicillin and grown 3 to 4 hours until the optical density at 600 nm reached 0.5–1.0. The gene was expressed by activating the tac promoter by the addition of isopropyl-b-D-thiogalactoside (IPTG, Sigma Chemical Co., St. Louis, Mo.) at a final concentration of 1 mM. Cells were harvested 30 minutes after induction at 37° C. Cell lysates were prepared and the soluble fraction of the lysates was obtained by centrifugation at 12,000×g for 20 minutes. The glutathione S-transferase (GST)-mosaic proteins were purified by affinity chromatography using glutathione sepharose 4B column (Pharmacia Biotech, Piscataway, N.J.).

Immunoblot Assay

Aliquots of each lysate or aliquots of the purified GST-mosaic proteins were subjected to electrophoresis on 12% polyacrylamide gels containing SDS (SDS-PAGE) followed by blotting onto a nitrocellulose membrane. Following protein transfer, the nitrocellulose membranes were incubated with blocking solution (0.1 M phosphate-buffered saline containing 1% bovine serum albumin, 0.5% Tween 20, and 10% normal goat serum) overnight at 4° C., and then incubated with human HCV positive sera diluted 1:100 or 1:200 in blocking solution for 1 hour at room temperature. For immunodetection, the membranes were washed three times with blocking solution, followed by the addition of affinity-purified goat anti-human immunoglobulin G (IgG) conjugated to horseradish peroxidase (Bio-Rad, Richmond, Calif.) diluted 1:4000 or 1:6000 in blocking solution, and incubated 1 hour at room temperature. After washing the membranes with blocking solution three times, diaminobenzidine (Sigma Chemical Co., St. Louis, Mo.) and hydrogen peroxidase were added to detect the presence of the horseradish peroxidase (HRP) reporter molecule.

Enzyme Immunoassay (EIA)

One hundred microliters of the purified full length fusion NS4 mosaic protein (GST-W3) was adsorbed to microtiter wells (Immuno II; Dynatech Laboratories, Inc., Chantilly, Va.) at a concentration of 100 ng/ml in 0.1 M phosphate-buffered saline, pH 7.5, overnight at room temperature. The microtiter wells were then incubated with human anti-HCV negative or positive sera diluted 1:500 in blocking solution (as described above for the immunoblot assay) for 1 hour at 37° C. After washing the microtiter wells, goat anti-human immunoglobulin G (IgG) conjugated to HRP diluted 1:4000 was added and incubated for 1 hour at 37° C. After washing the microtiter wells 5 times, substrate and chromophore was added (Abbott Diagnostics Division, North Chicago, Ill.) and incubated in the dark for 30 minutes. The reaction was stopped with acid and the optical density was measured at 493 nm.

Human Sera

Anti-HCV positive sera were obtained from Boehringer Mannheim Inc. (Penzberg, Germany) and from Boston Biomedical Inc. (West Bridgewater, Mass.). Anti-HCV negative sera were obtained from a collection of normal human blood donors reposited at the Centers for Disease Control and Prevention (CDC, Atlanta, Ga.). All sera were confirmed as anti-HCV positive or negative by EIA and initially reactive specimens were confirmed and further characterized by the supplemental test MATRIX immunoassay (Abbott Laboratories, Abbott Park, Ill.).

Gene Assembly

Figure 19:
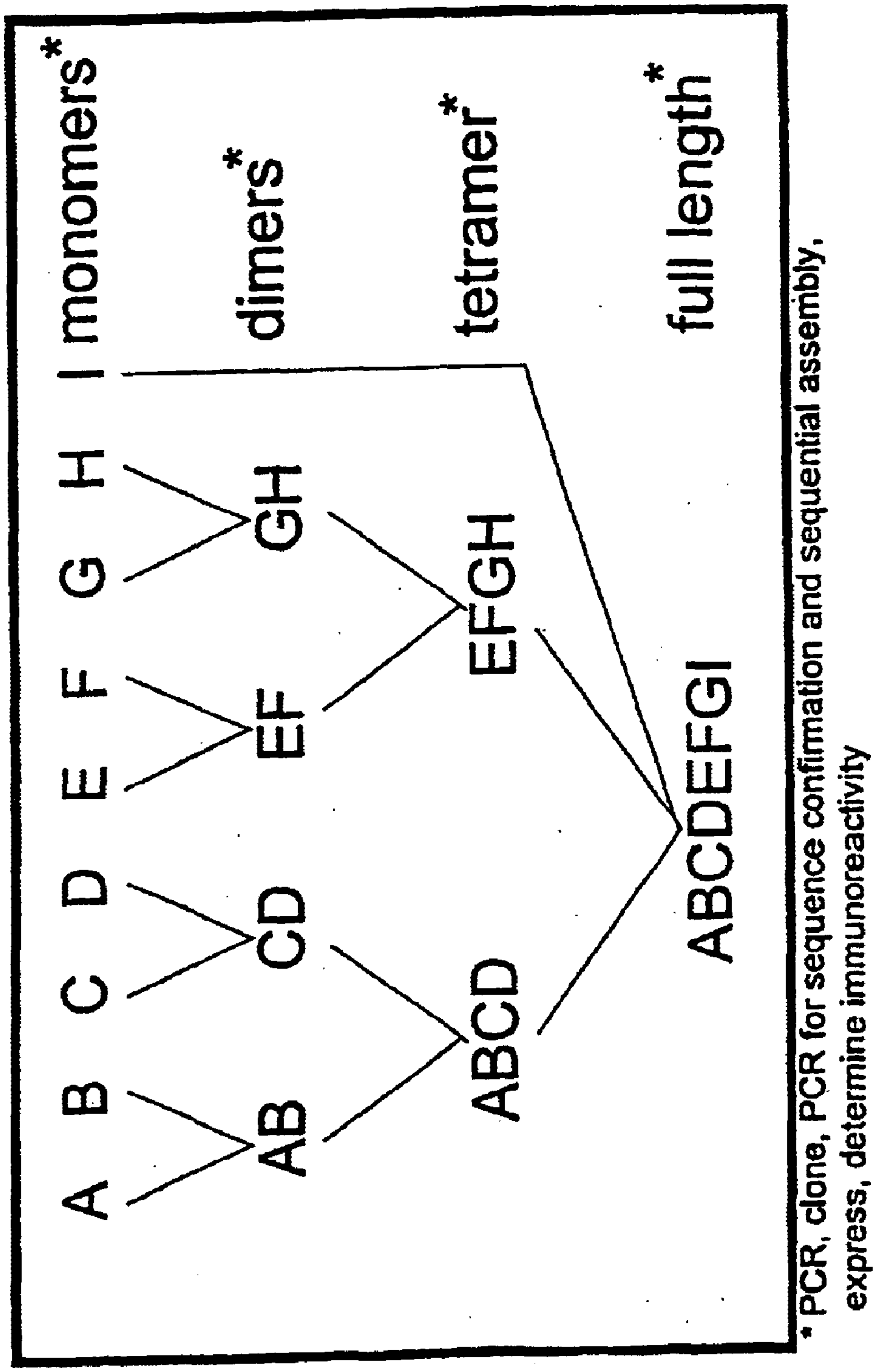
FIG. 19 demonstrates the strategy of NS4 gene assembly by Restriction Endonuclease Assisted Ligation (REAL). The mosaic NS4 gene was assembled from 9 consecutive monomers (A, B, C, D, E, F, G, H, and I). The monomers were first assembled into 4 dimers (AB, CD, EF, and GH), and then 4 dimers were further assembled into 2 tetramers (ABCD and EFGH). The full length gene was constructed by the ligation of 2 tetramers and 1 monomer (I).

The full length artificial NS4 mosaic gene was constructed in sequential steps from synthetic oligonucleotides by REAL. As shown in FIG. 19, each pair of oligonucleotides were converted into 9 monomers (A, B, C, D, E, F, G, H, and I), which were then consecutively assembled into 4 dimers (AB, CD, EF, and GH). Consecutive dimers were then assembled into 2 tetramers (ABCD and EFGH). The final gene was assembled from the 2 tetramers and the remaining monomer (I).

Gene Expression and Immunoblot Assay

Figure 20:
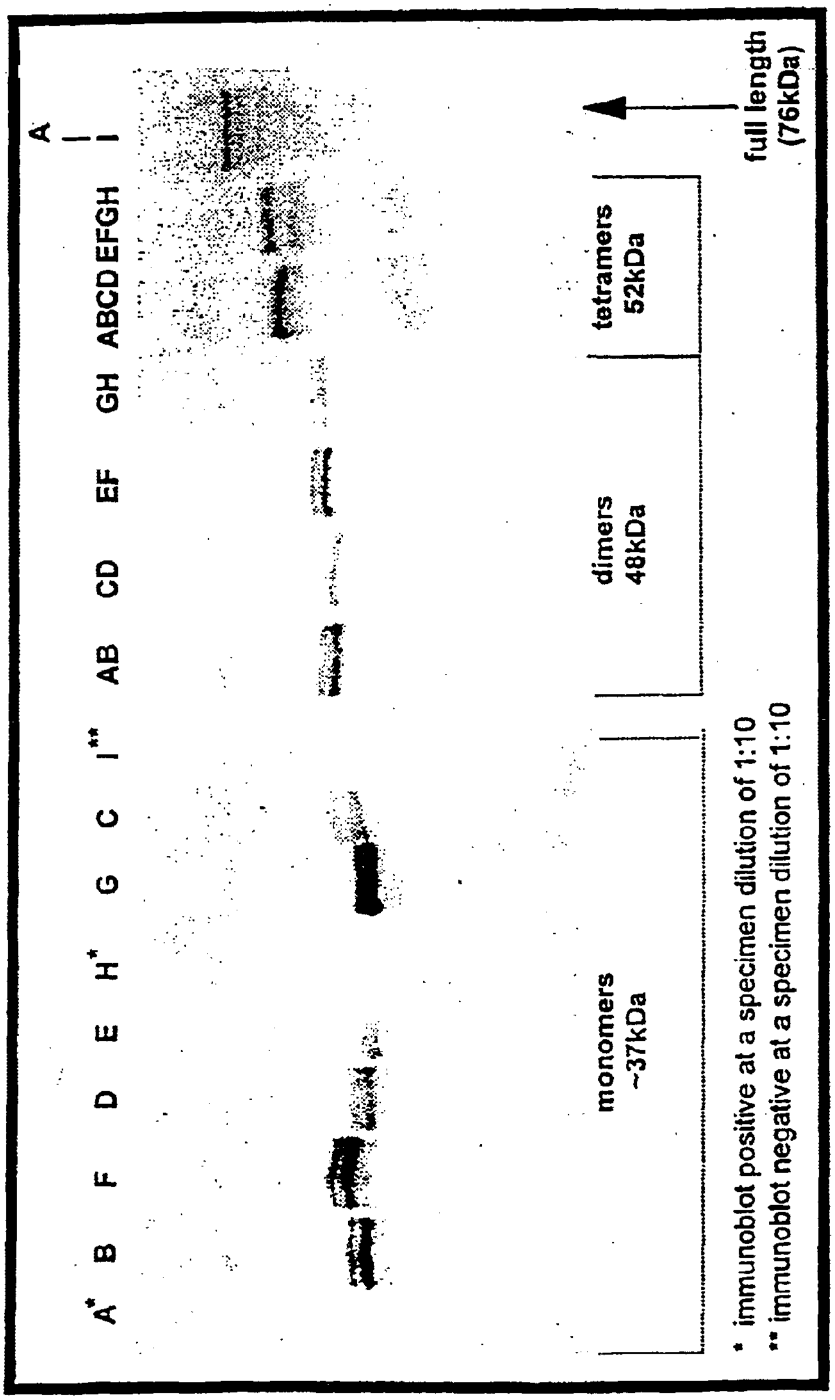
FIG. 20 shows the analysis of expressed and affinity-chromatography purified proteins of all monomers (A, B, C, D, E, F, G, H and I), dimers (AB, CD, EG, and GH), tetramers (ABCD, and EFGH), and the full length gene (A–I) by immunoblot using a single anti-NS4 positive specimen diluted 1:200. Three monomers (A, H, and I) were not immunoreactive even when the specimen was diluted 1:10.

SDS-PAGE analysis demonstrated that each fragment (9 monomers, 4 dimers, 2 tetramers, and the full length gene) was expressed at high levels following induction for 5 hours at 37° C. with 1 mM IPTG. Each of the expressed fragments and the expressed full length gene were purified by ligand affinity chromatography. All of the purified proteins were shown to be highly purified by SDS-PAGE, although many of the purified proteins displayed an artifactual doublet. In addition, each of the purified proteins were analyzed by immunoblot (FIG. 20) to ascertain individual immunoreactivity to human anti-HCV positive sera. The immunoblot showed that most of the purified proteins were strongly immunoreactive with a single anti-HCV positive specimen diluted 1:200. Three monomers (A, H, and I), however, were not immunoreactive using this specimen diluted 1:200. Monomers A and H were immunoreactive using pooled sera diluted 1:10 indicating that these monomers were immunoreactive. Monomer I demonstrated weak immunoreactivity by EIA.

NS4 Mosaic EIA Frequency Distribution

Figure 21:
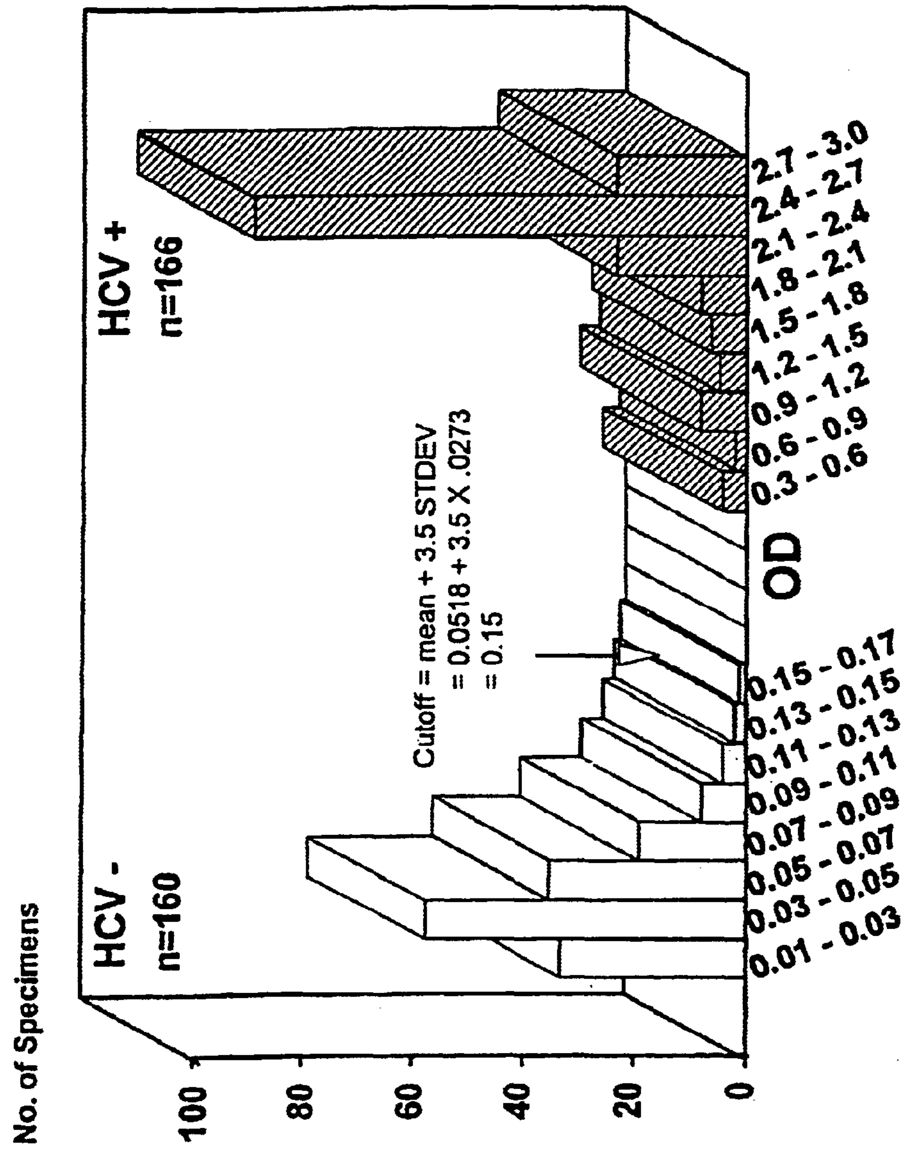
FIG. 21 depicts the frequency distribution of 160 anti-HCV negative sera and 166 anti-HCV positive sera by NS4 Mosaic EIA.

A statistically valid cutoff value was determined by screening 160 anti-HCV negative sera and 166 anti-HCV positive sera (anti-NS4 positive by MATRIX immunoassay) by EIA. The results showed that approximately 90% of anti-HCV negative sera gave OD values less than 0.09, while approximately 80% of anti-HCV positive sera gave OD values greater than 2.1. The mean OD value for the anti-HCV negative specimens was 0.0518±0.0273 standard deviations (SD). The cutoff value was established as the mean of OD values for anti-HCV negative sera plus 3.5 times the SD of the mean. This cutoff value unambiguously separated the negative sera from the positive sera (FIG. 21), although one negative specimen gave an OD value slightly above this cutoff. Using this cutoff value, all of the anti-HCV positive specimens tested positive by the NS4 Mosaic EIA. A two by two analysis of the data revealed a sensitivity of 100% and a specificity of 99.4% using this derived cutoff value. By raising the cutoff to the mean+4.3 times the SD, the specificity compared to MATRIX immunoassay was 100%.

Figure 22A:
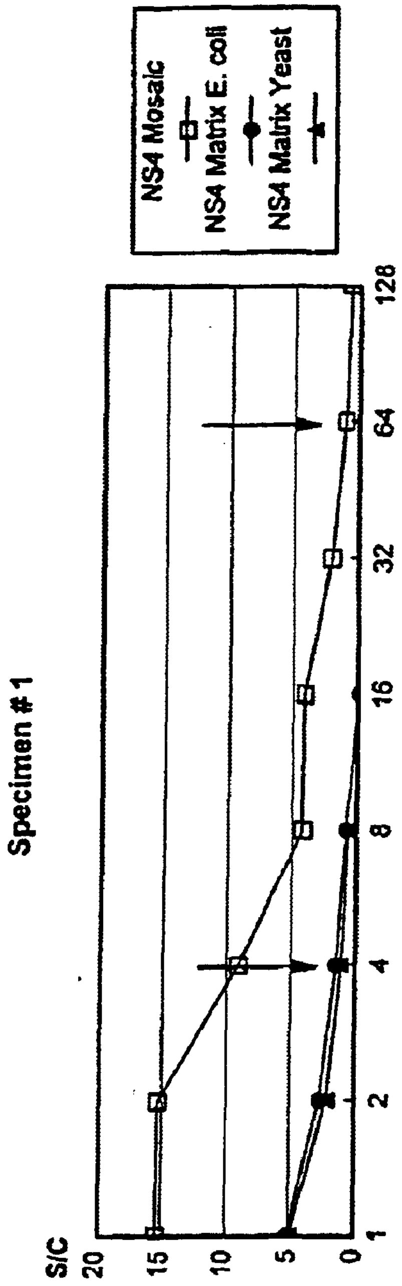
FIGS. 22A–B shows the endpoint titration of specimen no. 1 (FIG. 22A) and no. 2 (FIG. 22B) by the NS4 Mosaic EIA and by MATRIX immunoassay.
Figure 22B:
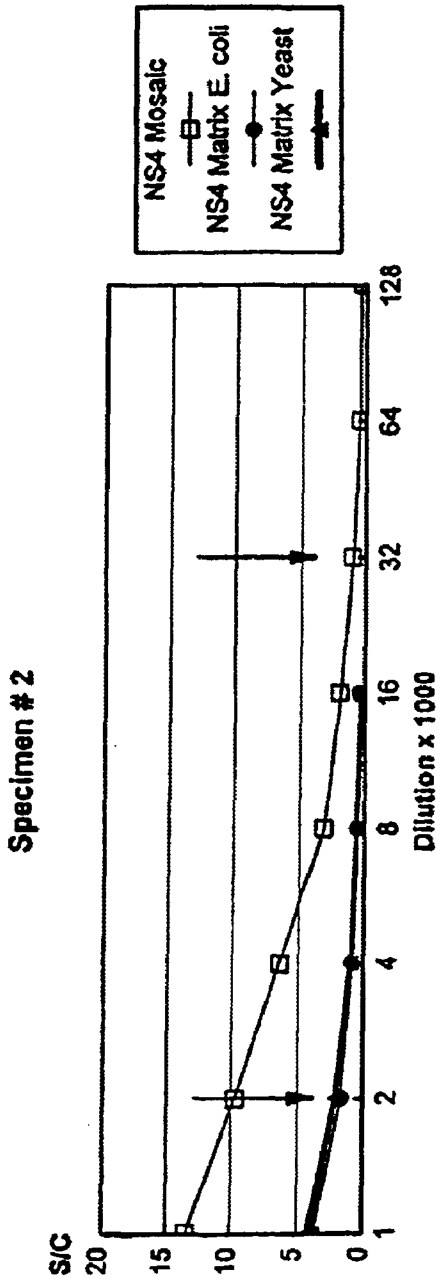
Figure 24A:
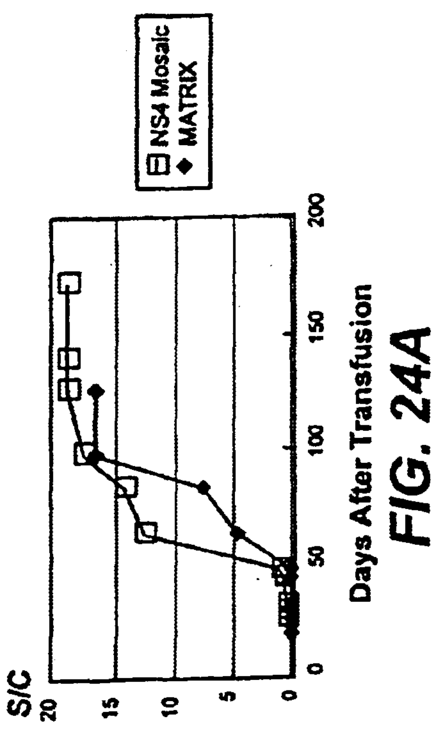
FIGS. 24A–D demonstrate the sensitivity of the NS4 Mosaic EIA versus MATRIX immunoassay for the detection of anti-NS4 activity in seroconversion panel nos. 4811 (FIG. 24A), 4812 (FIG. 24B), 6214 (FIG. 24C) and 4813 (FIG. 24D).
Figure 24C:
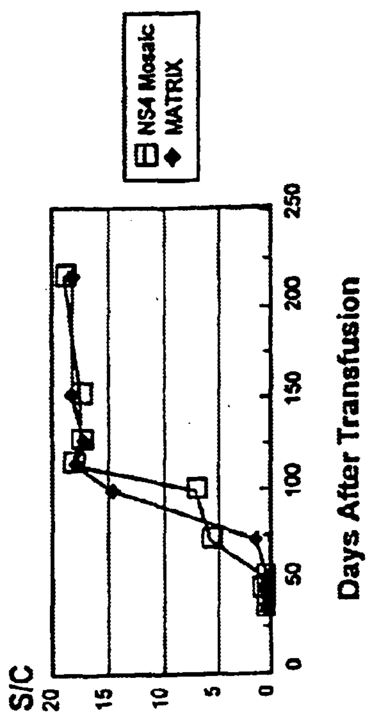
Figure 24B:
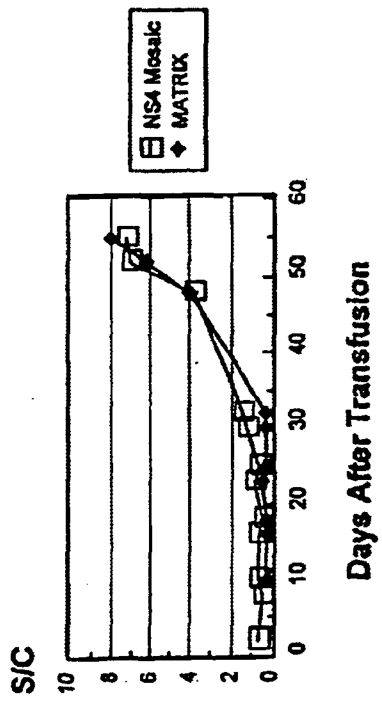
Figure 24D:
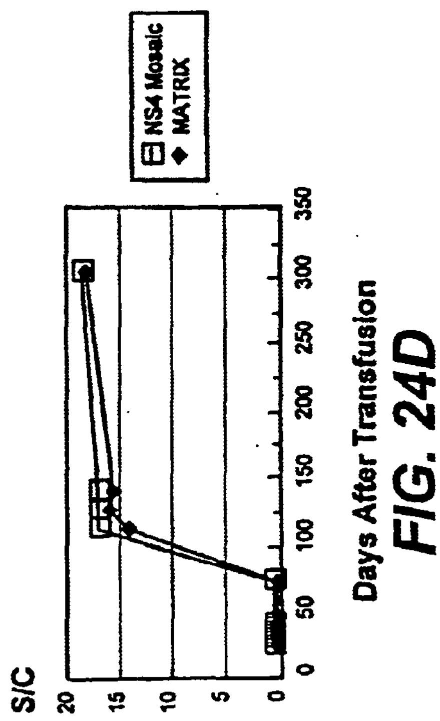

NS4 Mosaic EIA Compared to MATRIX Immunoassay on Serially Diluted Anti-HCV Positive Sera To examine the antigenic reactivity of the NS4 mosaic protein in detecting anti-NS4 activity, two serially diluted anti-NS4 positive sera were tested by the NS4 Mosaic EIA and by MATRIX immunoassay. The results showed that anti-NS4 antibody can be detected by the NS4 Mosaic EIA at a dilution of 1:128,000 times, while MATRIX immunoassay was positive for anti-NS4 activity at a dilution of approximately 1:4000. MATRIX immunoassay utilizes two different NS4 proteins expressed in *E. coli* and in yeast. This comparison indicated that the antigenic reactivity to the NS4 mosaic protein was 32 times more sensitive than MATRIX immunoassay for specimen no. 1 (FIG. 22A) and 18 to 25 times more sensitive for specimen no. 2 (FIG. 22B).

NS4 Mosaic EIA Compared to MATRIX Immunoassay for the Detection of Anti-HCV

Among 182 anti-HCV positive sera, 97.8% tested positive for anti-NS4 activity by the NS4 Mosaic EIA compared to 86.8% by MATRIX immunoassay. These results strongly suggest that the mosaic protein is a more sensitive immunologic target than either of the NS4 antigens used by MATRIX immunoassay. Antibody activity to the NS3 and nucleocapsid (NC) antigens by MATRIX immunoassay were also compared to the mosaic protein for anti-NS4 activity. This analysis showed that 98.4% of the 182 sera tested positive for anti-NS3 and 94.5% for anti-NC indicating that the NS4 Mosaic EIA is more sensitive than MATRIX immunoassay for anti-NC activity, and almost as sensitive as MATRIX immunoassay for anti-NS3 activity (FIG. 23).

NS4 Mosaic EIA Compared to MATRIX Immunoassay for Seroconversion Panels

Ten seroconversion panels (BioClinical Partners, Inc.; Serologicals, Chamblee, Ga.) were tested by the NS4 Mosaic EIA and by MATRIX immunoassay to determine the temporal appearance of anti-NS4 activity in recently infected individuals. The results showed that the NS4 Mosaic EIA detected anti-NS4 activity approximately 15 (FIG. 24) to 25 days (FIG. 24) earlier than MATRIX immunoassay when a cutoff value of at least 2.5 times background was used. In some cases, the NS4 Mosaic EIA and MATRIX immunoassay gave similar results; however, MATRIX immunoassay results never demonstrated earlier detection of anti-NS4 activity than NS4 Mosaic EIA results (data not shown). These results indicate that the NS4 mosaic protein, when used as the immunologic target in an EIA, was at least as sensitive as MATRIX immunoassay for the early detection of anti-NS4 activity, and probably more sensitive if more frequent bleed dates were available for each of the ten seroconversion panels.

NS4 Mosaic EIA Reactivity to Different HCV Genotypes

Figure 25:
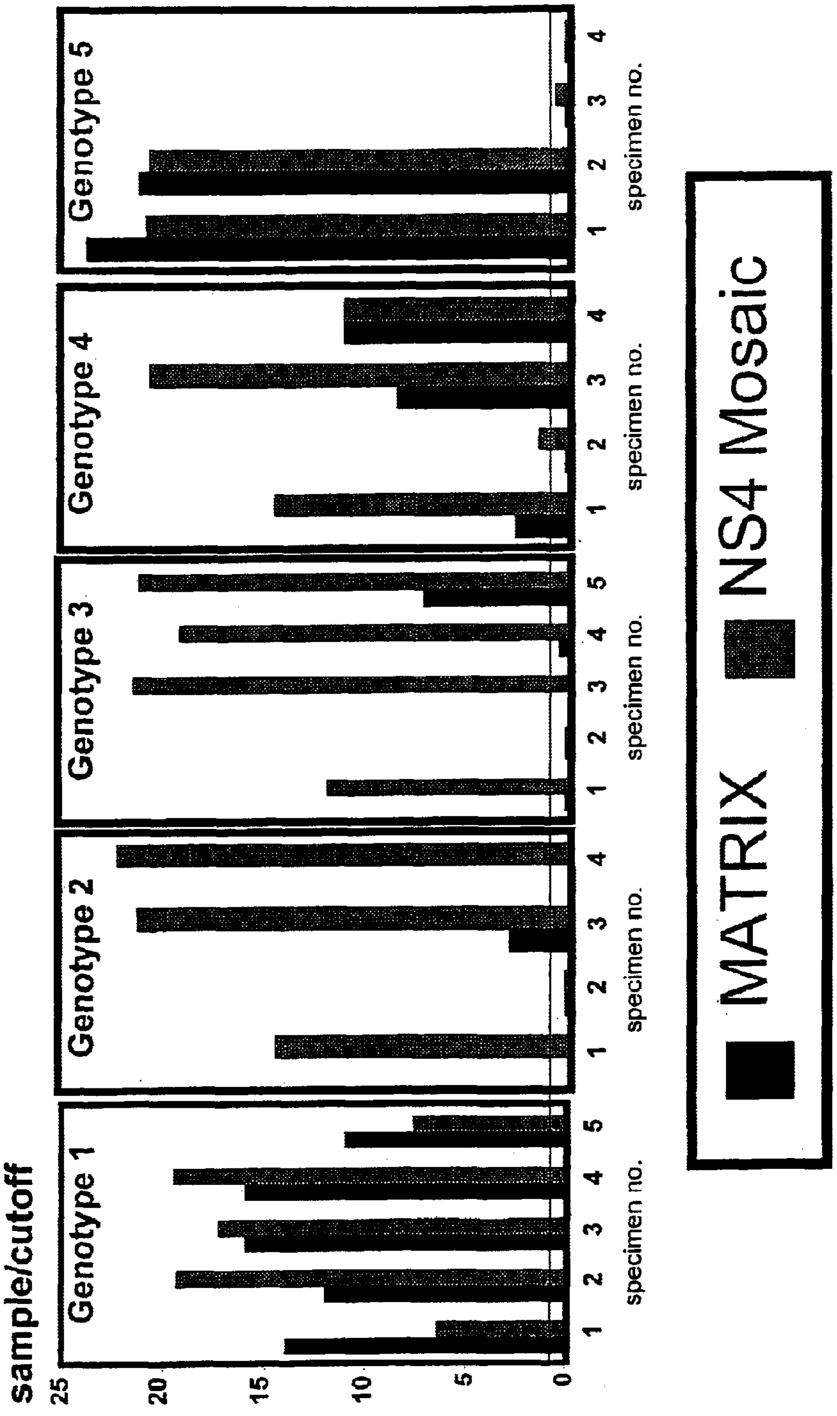
FIG. 25 shows the reactivity of genotype specific sera by NS4 Mosaic EIA for anti-NS4 activity.

Since the NS4 mosaic protein is composed of antigenic regions derived from several HCV subtypes and genotypes, it should detect anti-NS4 activity in the sera from patients infected with different genotypes. Genotypes 1–5 were tested for immunoreactivity by the NS4 Mosaic EIA. The results indicated that the only specimens which did not react to the mosaic protein were those that tested negative for anti-NS4 activity by MATRIX immunoassay. These data indicate that the mosaic protein detected anti-NS4 activity in each of the genotypes tested and was 100% concordant with MATRIX immunoassay (FIG. 25).

What is claimed is:

1. A nucleic acid encoding a mosaic protein comprising more than two antigenic peptides from the same domain from different genotypes of hepatitis C virus and wherein the mosaic protein comprises the amino acid sequences set forth in SEQ ID NOs:23–33.

2. A nucleic acid encoding a mosaic protein comprising more than two antigenic peptides from the same domain from different genotypes of hepatitis C virus, wherein the antigenic peptides are from non-structural proteins, and wherein the mosaic protein comprises the amino acid sequence set forth in SEQ ID NO:52.

3. A nucleic acid encoding a mosaic protein comprising more than two antigenic peptides from different genotypes or subtypes of Hepatitis C virus, wherein the antigenic peptides are selected from the amino acid sequences set forth in SEQ ID NOs:23–33.

4. The nucleic acid of claim 3, wherein the encoded mosaic protein comprises the amino acid sequences set forth in SEQ ID NOs:23–33.

5. The nucleic acid of claim 3, wherein the encoded mosaic protein comprises the amino acid sequences set forth in SEQ ID NOs:23–33 in numerical order in said mosaic protein.

6. A nucleic acid encoding a mosaic protein comprising more than two antigenic peptides from different genotypes or subtypes of Hepatitis C virus, wherein the encoded mosaic protein has an amino acid sequence set forth in SEQ ID NO:52.

* * * * *